United States Patent
Matsumoto et al.

(10) Patent No.: US 7,782,451 B2
(45) Date of Patent: Aug. 24, 2010

(54) DEVICE FOR AND METHOD OF INSPECTING SURFACE CONDITION HAVING DIFFERENT CURVATURES

(75) Inventors: Toshihiko Matsumoto, Kyoto (JP); Hiroshi Okabe, Kyoto (JP); Takashi Kinoshita, Kyoto (JP); Yoshihiro Kanetani, Kyoto (JP)

(73) Assignee: OMRON Corporation, Kyoto (JP)

( * ) Notice: Subject to any disclaimer, the term of this patent is extended or adjusted under 35 U.S.C. 154(b) by 403 days.

(21) Appl. No.: 11/707,293

(22) Filed: Feb. 14, 2007

(65) Prior Publication Data

US 2007/0211240 A1    Sep. 13, 2007

(51) Int. Cl.
*G01N 21/00* (2006.01)
(52) U.S. Cl. .................. 356/237.2; 356/237.1
(58) Field of Classification Search ... 356/237.1–237.2, 356/239.7, 612, 601, 402–425
See application file for complete search history.

(56) References Cited

U.S. PATENT DOCUMENTS

| | | | |
|---|---|---|---|
| 6,763,131 B1 * | 7/2004 | Shimada et al. | 382/151 |
| 2002/0030811 A1 * | 3/2002 | Schindler | 356/318 |
| 2004/0085544 A1 * | 5/2004 | De Groot | 356/497 |

FOREIGN PATENT DOCUMENTS

| | | |
|---|---|---|
| DE | 102004007829 | 9/2005 |
| GB | 2262339 | 6/1993 |
| JP | 06-160066 | 7/1994 |
| JP | 11-326235 | 11/1999 |
| JP | 2003-075363 | 12/2003 |
| WO | PCT/GB05/002783 | * 1/2006 |

OTHER PUBLICATIONS

EP patent application No. 07001425-1524, European Search Report dated Jun. 25, 2007.

* cited by examiner

*Primary Examiner*—Tarifur Chowdhury
*Assistant Examiner*—Michael LaPage
(74) *Attorney, Agent, or Firm*—Weaver Austin Villeneuve & Sampson LLP

(57) ABSTRACT

A target surface of a target object including portions having different curvatures is inspected by using an illuminating device and a camera that are fixed, a supporting device for supporting the target object such that its position and orientation are variable. The position and orientation of the target object are controlled as its image is obtained for a plurality of times. The position and orientation of the target object are controlled such that the image of any point on the target surface will be included in at least one of the images obtained by the camera.

6 Claims, 18 Drawing Sheets

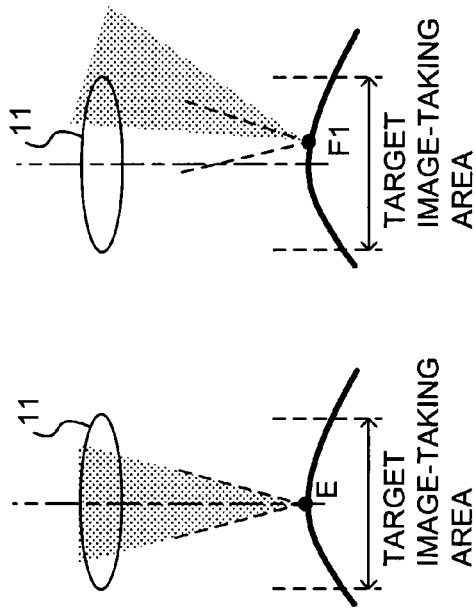
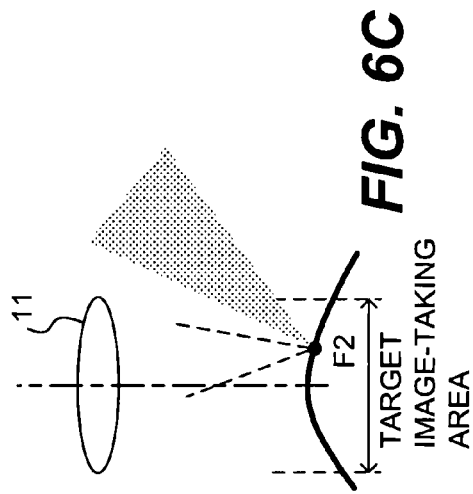
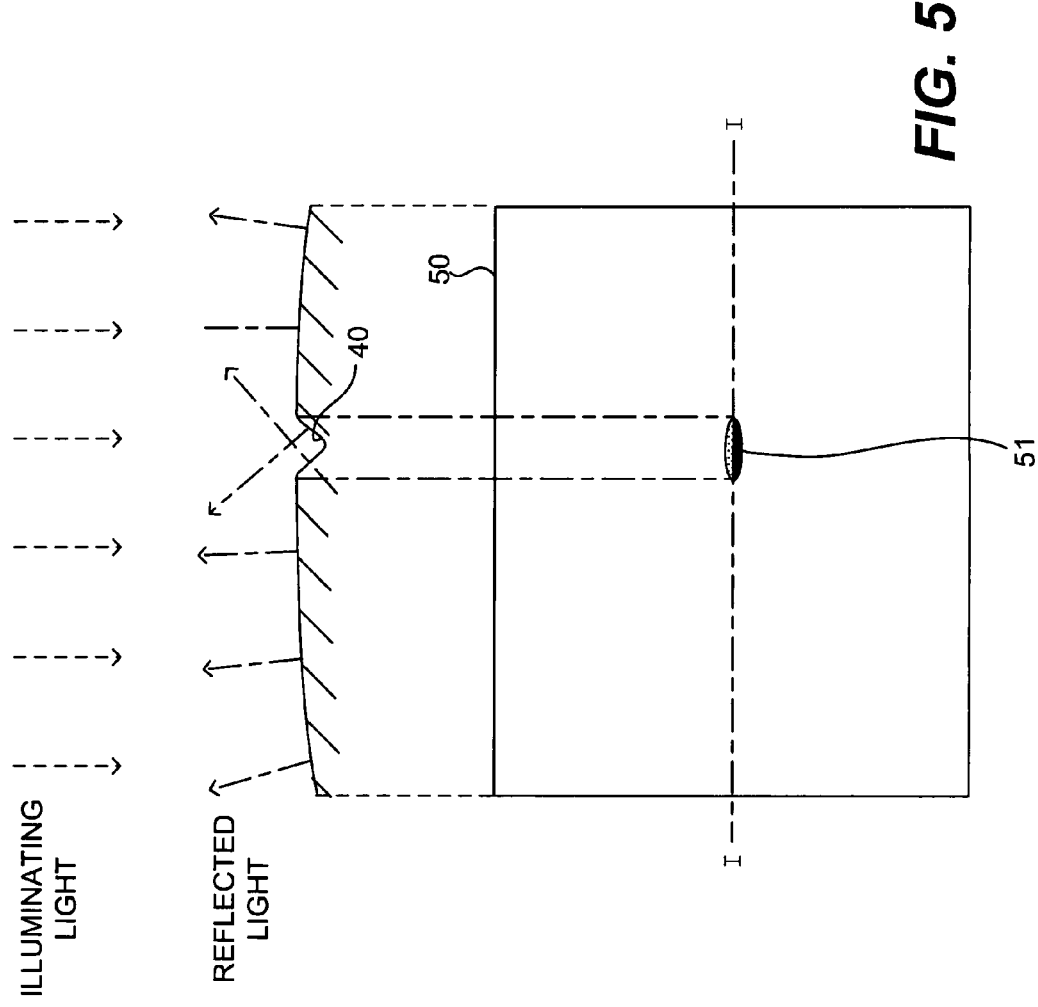

DEVICE FOR AND METHOD OF INSPECTING SURFACE CONDITION HAVING DIFFERENT CURVATURES

This application claims priority on Japanese Patent Application 2006-066081 filed Mar. 10, 2006.

BACKGROUND OF THE INVENTION

This invention relates to a device for and a method of inspecting the surface of a target object having a specified shape. More particularly, this invention relates to such device and method by taking an image of a target surface by illuminating it from a specified direction and processing an image by regularly reflected light in the generated image.

As a method of defecting surface unevenness of a target object, it has been known to set a camera at a position where regularly reflected light from the target surface can be made incident while this target object is being illuminated from a specified direction. Japanese Patent 2923808, for example, describes a method of detecting the surface unevenness of a glass substrate having a flat surface and Japanese Patent Publication Tokkai 2003-75363 describes a method of detecting defects on the peripheral surface of a cylindrical photosensitive body for electron photography.

If the target surface is of a certain size, it is not possible of obtain the image of the entire surface at once. In such a situation, the camera and the device for the illumination must be moved with respect to the target object. Aforementioned Japanese Patent 2923808 describes the use of an XY moving mechanism for moving the target object parallel to the target surface of inspection and partitioning the target surface into a plurality of areas. Aforementioned Japanese Patent Publication Tokkai 2003-75363 describes the method of rotating the target object around its longitudinal axis to obtain its images.

In recent years, however, fashionable products such as portable telephones and portable music players are frequently designed by combining free-shaped surfaces with different curvatures. Surface conditions of such products, too, are required to be inspected after their production or before their shipment. In order to improve their product value, makers are coming to demand an inspection of a high level. It is extremely difficult, however, to carry out an inspection of the kind using regularly reflected light over the entire surface of a product with portions having different radii of curvature.

SUMMARY OF THE INVENTION

It is therefore an object of this invention in view of the problem described above to make it possible to carry out an inspection based on regularly reflected light even in the case of a target surface having portions with different radii of curvature.

A method of this invention is for inspecting the condition of a target surface of a target object including portions having different curvatures by obtaining an image of the target surface by regularly reflected light for a plurality of times and processing the obtained images of the target surface. For obtaining these images, use is made of an illuminating device and a camera that are fixed, and the target object is supported such that its position and orientation are variable.

A preparation is carried out preliminarily for sequentially inspecting a plurality of target objects having a same shape by determining the position and orientation that are to be taken by each of the target objects each time and determining target inspection areas on the obtained images to thereby generate set data that represent the results of the preparation. The image of the target surface is obtained by supporting the target object in the position and orientation according to the set data, and the position and orientation of the target objects and the target inspection areas are determined such that each of the target inspection areas is determined as the area where the corresponding image by regularly reflected light is obtained or a portion of the area and that the image of any point on the target surface will be included in at least one of the target inspection areas of any of the obtained images obtained.

In the above, the set data representing the position and orientation to be taken by the target object are not limited to data that directly represent the position and orientation of the target object but may also include those data that indirectly represent the position and orientation of the target object such as data representing the position of target image-taking points on the target object and the directions in which images of such points are to be taken. The position and orientation of the target can be identified as these data are used together with otherwise obtainable data on the positioning and operation control of devices used for the inspection such as the camera and the supporting means for the target.

The target inspection area means the area within an image where an inspection is to take place. An inspection will be carried out at least on the target inspection area but it is not prevented to carry out an inspection (or an image processing for an inspection) on a part other than the target inspection area. If an inspection is limited to the target inspection area, however, the inspection time may be reduced because the amount of calculations to be carried out for the image processing becomes less.

The area where an image by regularly reflected light is to be obtained means the area where it is expected to be possible to observe the arrival of regularly reflected light on the image obtained by an image-taking process. The arrival of regularly reflected light can be recognized by the quantity of received light over a threshold value.

By a method thus described, the whole of a target surface of a target object including portions having different curvatures can be inspected based on images by regularly reflected light.

According to a preferred embodiment of the invention, the aforementioned preparation is carried out by using the camera to obtain a so-called model image of a model object considered to have no defects, supported such that its position and orientation are variable, while the model image is being displayed on a monitor. In the preparation, what is herein referred to as the first setting unit process is carried out on a plurality of specified places on a target inspection surface of the model object serving as target object and these specified places are specified such that the image of any point on the target surface is included in at least one of the plurality of target inspection areas determined by carrying out this first setting unit process.

In the above, the first setting unit process is characterized as comprising step A of determining the position and orientation of the target object such that an image including the image by regularly reflected light of a specified place on a target inspection surface of the target object will be displayed on the monitor, step B of determining the area on the image of the target area on which the image by regularly reflected light is obtained or a portion of the area as the target inspection area, and step C of generating set data representing the position and orientation determined in step A and the target inspection area determined in step B.

By thus using a model object which is a real object believed to have no defect, set data representing the position and orientation of a target object as well as target inspection area to be used at the time of carrying out an inspection can be easily generated.

According to another preferred embodiment of the invention, the aforementioned preparation is carried out by using design data representing three-dimensional shape of the target object and carrying out what is herein referred to as the second setting unit process on a plurality of specified places on a target inspection surface of the target object wherein these specified places are specified such that the image of any point on the target surface is included in at least one of the plurality of target inspection areas determined by carrying out the second setting unit process.

In the above, the second setting unit process is characterized as comprising step a of using the design data and thereby obtaining the direction of the normal line to the target surface at a specified position, step b of using the design data and thereby identifying an area on the target object where regularly reflected light can be made incident to the camera if the camera takes an image of the specified position on the target surface along the normal line, step c of obtaining a regular reflection image area on the image taken in step b, the regular reflection image area being the area on which the area on the target object identified in step b appears, step d of determining the regular reflection image area or a portion of it as the target inspection area, and step e of generating set data that represent the position and orientation of the target object identified by the position of the specified position and the direction of the normal line obtained in step a and the target inspection area.

By thus using design data representing three-dimensional shape of the target object, set data representing the position and orientation of a target object as well as target inspection area to be used at the time of carrying out an inspection can be easily generated.

Another method of this invention for inspecting condition of a target surface of a target object is characterized wherein a camera and an illuminating device that are fixed are used to take an image of the target object for a plurality of times by sequentially changing its position and orientation such that the image of any point on the target surface will be included in a target inspection area of at least one of the plurality of obtained images.

By this method, too, the whole of a target surface of a target object including portions having different curvatures can be inspected based on images by regularly reflected light.

A device of this invention is for inspecting condition of a target surface of a target object including portions having different curvatures and may be characterized as comprising an illuminating device and a camera that are fixed, a supporting device for supporting the target object such that its position and orientation are variable, and a control device for controlling the position and orientation of the target object as its image is obtained for a plurality of times by the camera and by illuminating with the illuminating device. The position and orientation of the target object are controlled such that the image of any point on the target surface will be included in at least one of the images obtained by the camera.

By using such a device, the whole of a target surface of a target object including portions having different curvatures can be inspected based on images by regularly reflected light.

According to a preferred embodiment of the invention, the supporting device comprises an articulated robot arm having a plurality of shafts. The camera is fixed so as to be able of take images of the target object supported by the robot arm obliquely from above, and the control device serves to attach the target object to an end position of the robot arm as the target object is supplied to a position below the camera and to move the attached target object to another position where the camera can take an image of the target object.

With the positional relationship thus established between the camera and the robot arm, the optical axis of the camera can be pointed obliquely downward and the area for setting the device as a whole can be reduced as compared to a situation where the optical axis is horizontal. Since the distance by which the end of the robot arm must be moved to attach the target object can be reduced, the inspection time can also be reduced. Since the lens of the camera is also pointing downward, dust particles are not likely to accumulate thereon.

In summary, this invention makes it possible to carry out an inspection over the whole of a target surface of a target object, even if it includes portions having different curvatures, by using images by regularly reflected light.

BRIEF DESCRIPTION OF THE DRAWINGS

FIG. 5 is a drawing for explaining the principle of inspecting a surface defect.

FIGS. 6A, 6B and 6C are drawings for explaining the manners in which regularly reflected light is received or not received by the lens of the camera.

DETAILED DESCRIPTION OF THE INVENTION

Figure 1:
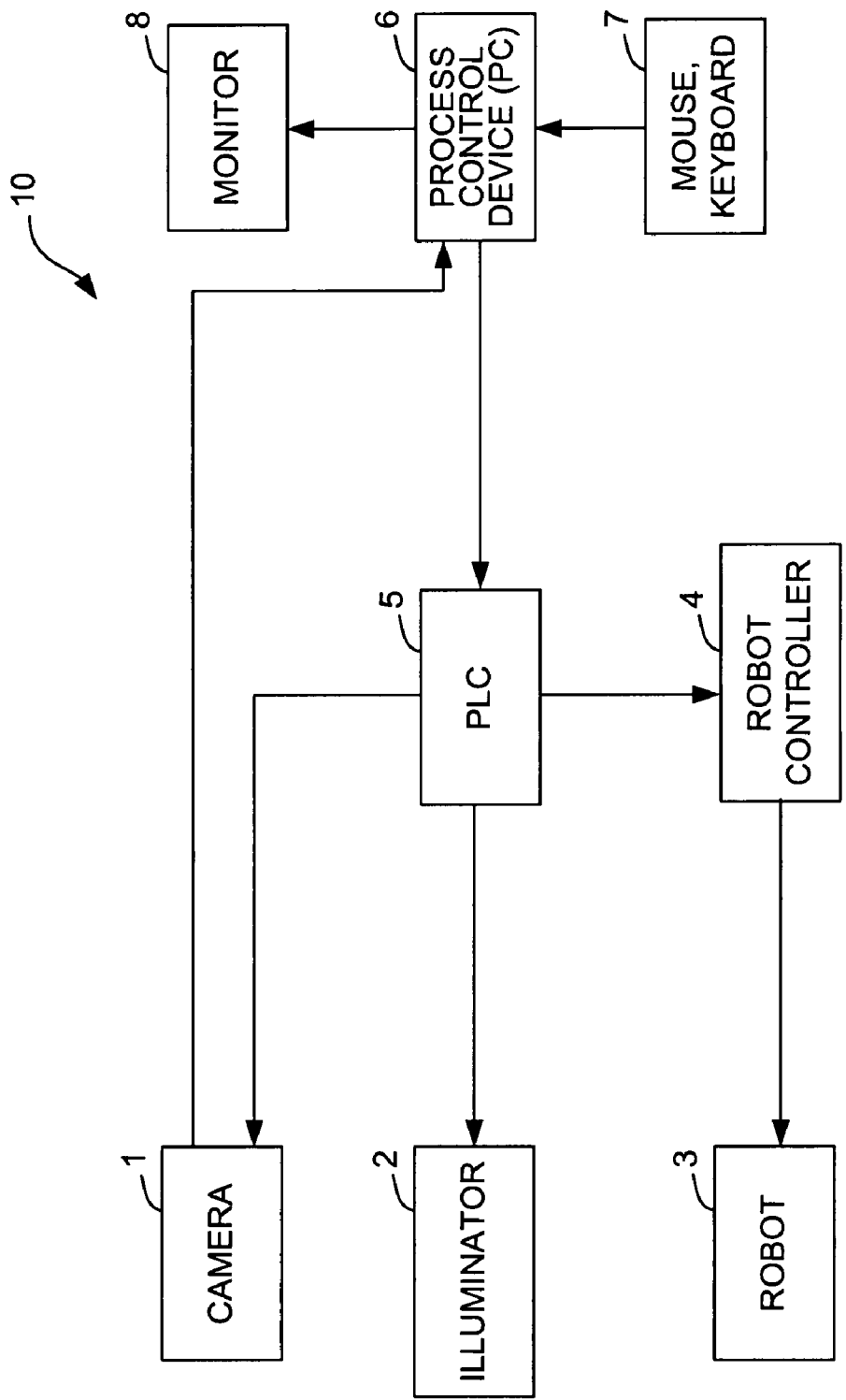
FIG. 1 is a block diagram of an inspection device embodying this invention.

FIG. 1 shows an inspection device 10 embodying this invention for detecting defective unevenness such as scratches on a molded product such as the casing of a portable telephone, as well as color defects such as contaminations. As shown, this inspection device 10 is provided with a camera 1, an illuminator 2, a robot 3 with six shafts, a robot controller 4, a programmable logic controller (PLC) 5 and a process control device 6. The process control device 6 comprises a personal computer in this example, having an input device 7 such as a mouse and a keyboard and a monitor 8 connected thereto.

The camera 1 is a digital still camera having a solid image-taking element such as CCD. The illuminator 2 is for illuminating a target object of inspection, including two kinds of illuminating parts 2A and 2B, as will be explained below. The robot 3 is for supporting the target object such that its image can be taken by the camera 1. Its motion is controlled by the robot controller 4.

Programs (written in the ladder language) for controlling the camera 1, the illuminator 2 and the robot controller 4 are installed in the PLC 5. The PLC 5 carries out these programs repeatedly with a specified frequency for inspecting a plurality of identically shaped target objects sequentially.

The PLC 5 is adapted to output a trigger signal to the camera 1 for taking an image and an illumination control signal to the illuminator 2 for switching the illumination. Data indicative of the position and direction of a target object are outputted to the robot controller 4. The robot controller 4 controls the rotary motion of each of the six shafts of the robot 3 based on the received data.

The control programs for the PLC 5 are created by the user by using the process control device 6. Conditions and parameters necessary for the inspection are similarly set. Completed control programs and data that have been set are transmitted from the process control device 6 to the PLC 5. Thereafter, the user (operator) uses the process control device 6 to provide the PLC 5 with instructions for starting and ending the execution of the control programs. During the inspection, the process control device 6 serves as a host to the PLC 5, monitoring its operations and taking in the image data generated by the camera 1 to carry out image processing for the inspection.

Figure 2:
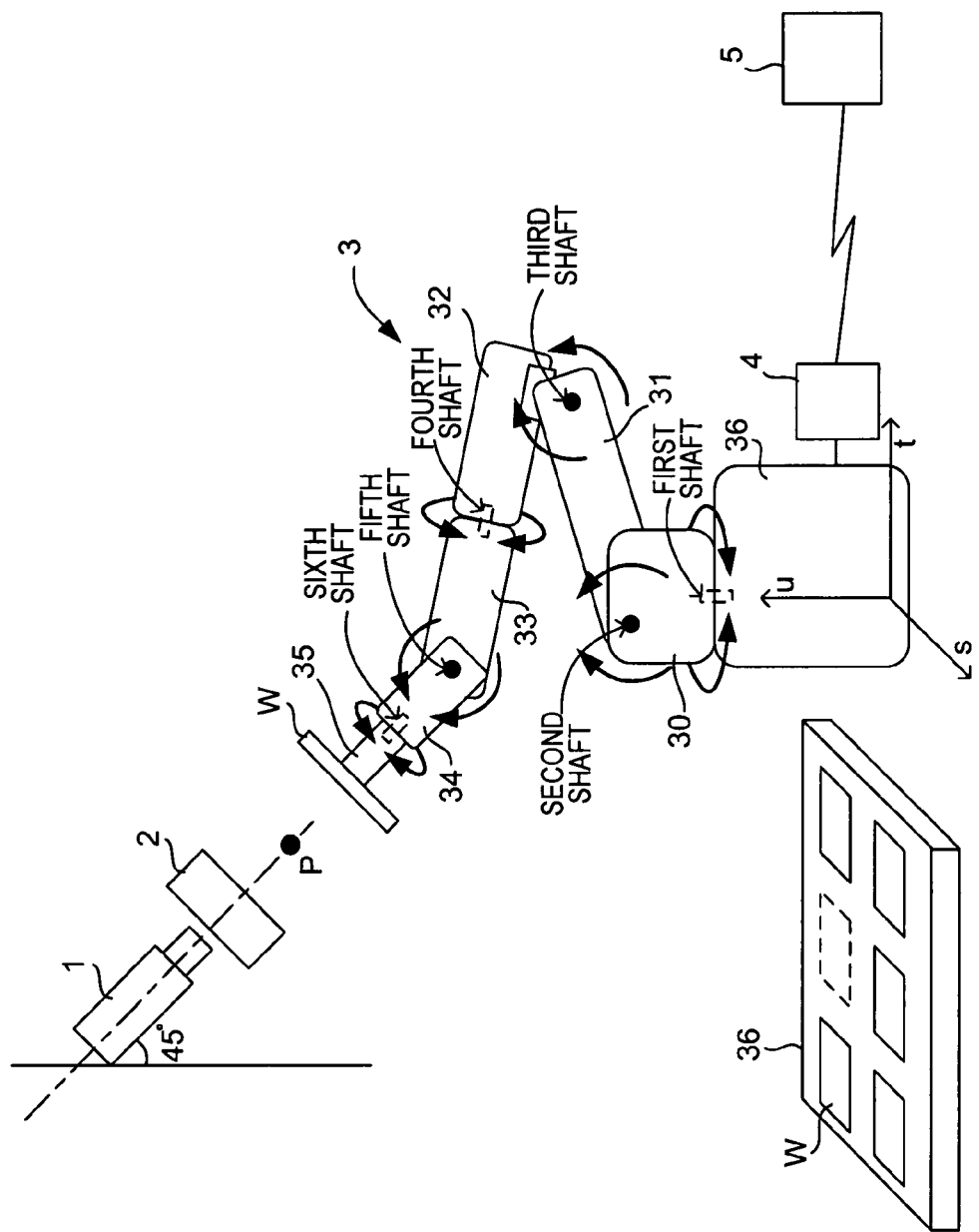
FIG. 2 is a drawing for showing the specific structure of the robot and its positional relationship with the optical system.

FIG. 2 shows the specific structures of the camera 1, the illuminator 2 and the robot 3, as well as their positional relationship at the time of inspection. In this example, the camera 1 is set with its optical axis directed diagonally downward (45° from the vertical) and the illuminator 2 is placed in front of it. The camera 1 and the illuminator 2 are each supported at a specified height by means of a supporting member (not shown), and their optical axes and focal distances are also fixed.

The robot 3 has an arm supporting part 30, four intermediate arms 31, 32, 33 and 34 an end arm 35 sequentially connected on top of a base 36 of a specified size. Each of the connecting parts includes a rotary shaft. In what follows, the four intermediate arms 31-34 are referred to as the first arm 31, the second arm 32, the third arm 33 and the fourth arm 34 in this order from the side of the base 36 towards the end arm 35. The rotary shafts at the connecting parts are similarly referred to as the first shaft, the second shaft, the third shaft, the fourth shaft, the fifth shaft and the sixth shaft from the side of the base 36 towards the end arm 35.

The first shaft connecting the base 36 with the arm supporting part 30 is in the vertical direction. The second shaft connecting the arm supporting part 30 with the first arm 31 and the third shaft connecting the first arm 31 with the second arm 32 are each set in the horizontal direction (perpendicular to the plane of the paper). The fourth shaft connecting the second arm 32 with the third arm 33 is in the longitudinal direction of these arms 32 and 33. The fifth shaft connecting the third arm 33 with the fourth arm 34 is perpendicular to the longitudinal direction of the third arm 33 and the fourth arm 34. The sixth shaft connecting the end arm 35 with the fourth arm 34 is in the longitudinal direction of the end arm 35 and the fourth arm 34.

Of these six shafts, the first, second and third shafts are mainly used to adjust the approximate position of the end arm 35 and the fourth, fifth and sixth shafts are mainly used to adjust its orientation.

A tray 36 is supplied to a position below the camera 1. A plurality of indentations (not shown) for accepting target objects of inspection are formed on the upper surface of the tray 36, and a target object is placed in each of these indentations with the back surface facing upward.

The robot 3 is at the center of the field of vision of the camera 1 and is arranged such that its end arm 35 can reach both the focal point of the camera 1 (hereinafter referred to as the standard image taking point P) and each of the indentations on the tray 36. A flange is provided at the end of the end arm 35, and this flange is further provided with a jig (not shown) provided with a vacuum adsorbing mechanism.

The robot 3 picks up the target objects in the tray 36 one by one by adsorption to the jig on the flange in response to an instruction from the robot controller 4, carrying them to the front of the camera 1. The position and orientation of each transported target object are changed thereafter by instructions from the robot controller 4.

According to this example, a spatial coordinate system is formed by three axes s, t and u for the control of the robot 3. The u-axis coincides with the aforementioned first shaft, and the s-axis and the t-axis are on the plane on which the robot 3 is set.

The tray 36 is supplied to a predetermined position on the st-plane in a predetermined orientation. The position of each indentation on the tray 36 is also fixed. On the basis of these conditions, the robot controller 4 adjusts the position and the orientation of the end arm 35 such that the target object will be supported thereby so as to be in the positional relationship shown in FIG. 3 when it is adsorbed.

Figure 3:
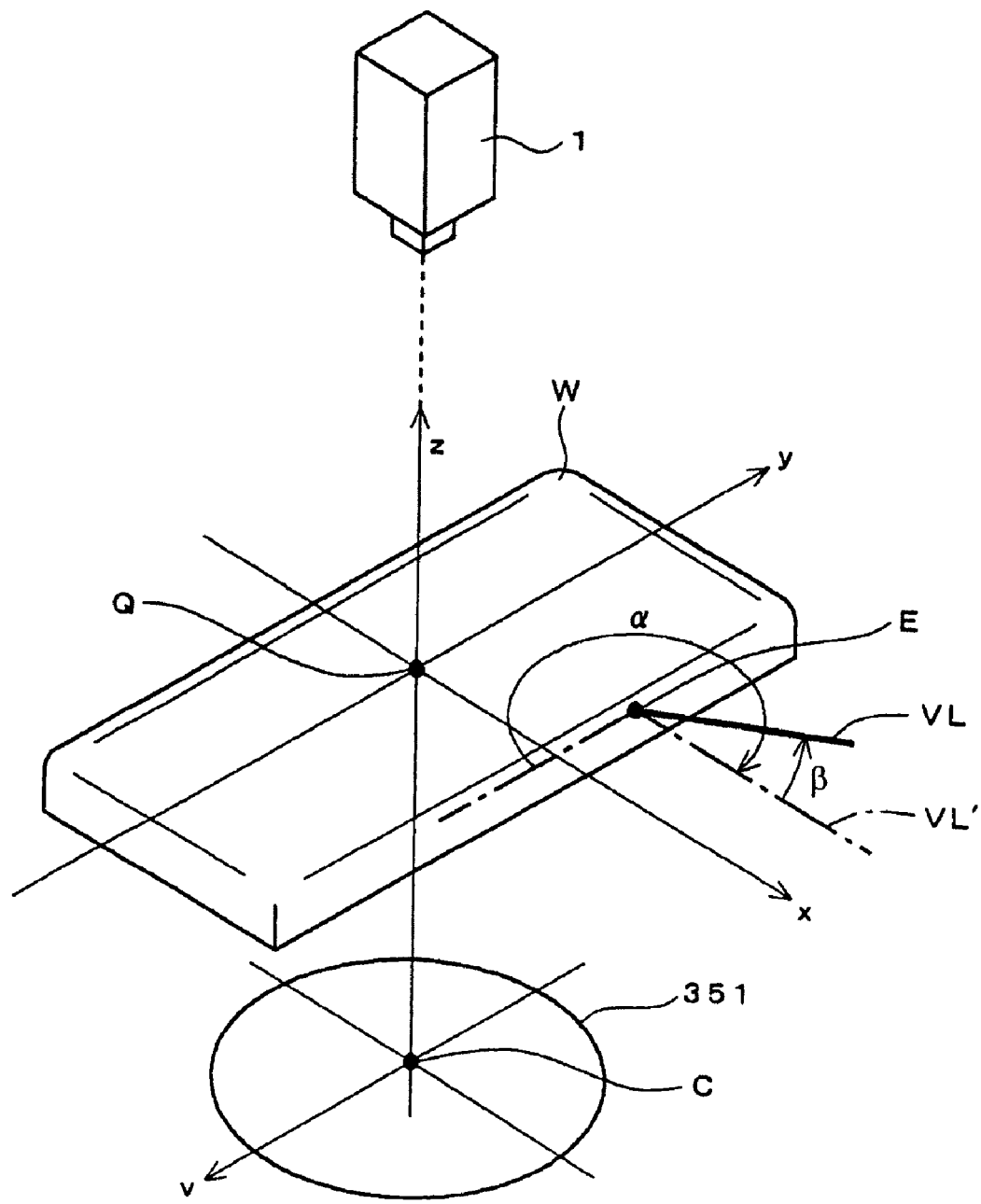
FIG. 3 is a drawing for showing the positional relationship among the end arm of the robot, a target object and the camera.

FIG. 3 shows the positional relationship among the end arm 35 of the robot 3, a target object W and the camera 1. Numeral 351 in the figure indicates the end surface of the flange (hereinafter referred to as the flange surface). Point C indicates the center of the flange surface which is on the line defined by the sixth shaft. Arrow v indicates a reference direction on the flange surface 351.

Another coordinate system defined by mutually orthogonal x-, y- and z-axes is fixed to the target object W. Q indicates the origin of this coordinate system. According to the illustrated example, the target object W is set such that the z-axis is colinear with the sixth shaft of the robot 3 (both C and Q being thereon) and the y-axis is in the direction opposite to arrow v. This positional relationship is maintained until the inspection of the target object W is finished. From this positional relationship, the distance between C and Q may be treated as known information.

Although FIG. 3 shows a target object as being flat and having a rectangular shape with rounded corners, objects with more complicated shapes, say, having a surface with portions with different radii of curvature can also be targeted. Even such objects may be mounted to the end arm 35 in a similar positional relationship.

Next, a point E on the target object W which is intended to be at the center when an image of the object W is taken by the camera 1 is considered. This point will be hereinafter referred to as the representative point and it will be assumed that an image is taken from the direction of the normal line VL at the representative point E. The position of the representative point E is expressed in the aforementioned xyz-system, and the direction of the normal line VL is expressed in terms of directional angle α and elevation angle β. If normal line VL is projected onto the xy-plane and VL' indicates the projected line, directional angle α is defined as the angle made by VL' from the direction of –y in the clockwise direction. Elevation angle β is the angle between normal line VL and its projection VL' on the xy-plane.

The coordinates x, y and z of the representative point E and the angles α and β defining the direction of normal line VL are provided to the robot controller 4 from the process control device 6 through the PLC 5. The robot controller 4 controls the rotary motion of each shaft of the robot 3 based on the provided data such that the representative point E will match the standard image taking point P and the normal line VL coincides with the optical axis of the camera 1. As explained above, the positional relationship between the target object W and the end arm 35 is known. The length of each arm of the robot 3 is known, and the angle of rotation of each shaft is recognized by the robot controller 4. Thus, the position of any point given by coordinates x, y and z can be expressed in the stu-coordinate system. It is also possible to obtain the rotary angles of the shafts in order to match the representative point E with the standard image taking point P and the direction of the normal line VL shown by angles α and β with the optical axis of the camera 1. After the position and orientation of the target object W are adjusted by the robot controller 4, an image is taken by the camera 1 and an image for inspection is generated.

Figure 4:
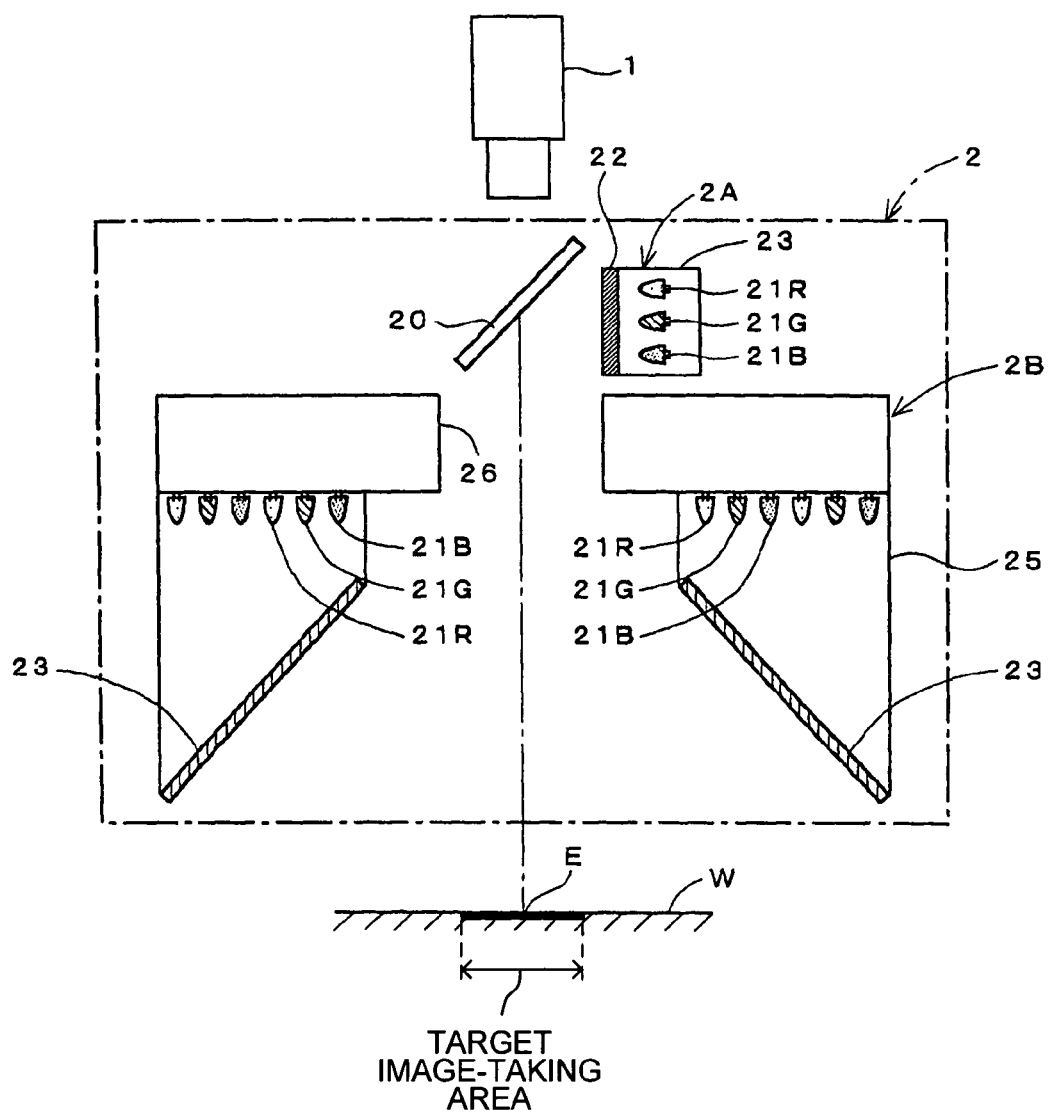
FIG. 4 is a schematic drawing of the optical system

FIG. 4 shows the structure of the optical system (the camera 1 and the illuminator 2) of the inspection device 10. It is to be reminded that the illuminator 2 is drawn larger with respect to the camera 1 for the convenience of description and that the optical axis of the camera 1 is in the up-down direction in the figure. The target object W is shown as a flat surface, and a target area on the target object W within the field of vision of the camera 1 is indicated. This area is hereinafter referred to as the "target image-taking area".

The illuminator has a half-mirror 20, a first illuminating part 2A for coaxial falling illumination and a second illuminating part 2B for illumination by oblique incidence incorporated therein. The half-mirror 20 is disposed on the optical axis of the camera 1. The first illuminating part 2A is at one side of the half-mirror 20, and the second illuminating part 2B is below the half-mirror 20.

The first illuminating part 2A for coaxial falling illumination has light sources (such as LEDs) 21R, 21G and 21B respectively for emitting red (R), green (G) and blue (B) light contained inside a box 23 having a circular opening (to the left in the figure) for projecting light therethrough. Each of the light sources 21R, 21G and 21B has its optical axis directed towards the half-mirror 20. The opening through the box 23 is equipped with a diffusing plate 22.

The second illuminating part 2B for illumination by oblique incidence has a plurality each of light sources 21R, 21G and 21B similarly to those of the first illumination part 2A arranged in circles inside a box 25 having a peephole 26 for the camera 1 on its upper surface. The optical axis of each of the light sources 21R, 21G and 21B is arranged to be parallel to the optical axis of the camera 1. The bottom of the box 25 is open and a light diffusing member 23 is disposed at this opening. This light diffusing member 23 has a conical or pyramid-shaped inner surface, the expanding side of this inner surface being directed towards the opening part of the box 25. The optical axis of the camera 1 passes through the center of the peephole 26.

Light from the light sources 21R, 21G and 21B of the first illuminating part 2A is mixed by the diffusing plate 22 to form a beam with a circular cross-sectional shape, which propagates along the optical axis of the camera 1 after reaching the half-mirror 20. Thus, if the first illuminating part 2A is switched on, so-called coaxial falling light of illumination irradiates the target image-taking area.

Light from the light sources 21R, 21G and 21B of the second illuminating part 2B is mixed inside the box 25 and projected through the light diffusing member 23 to the area below the peephole 26. Thus, if the second illumination part 2B is switched on, obliquely incident illuminating light irradiates the target image-taking area.

The diameters of incident light of both kinds are adjusted so as to cover the target image-taking area entirely. Both the first and second illuminating parts 2A and 2B are adapted to select the kinds of light sources to be switched on according to the color of the target object W.

According to the present example, an image is taken under the condition of coaxial falling illumination by the first illuminating part 2A when the presence or absence of defective unevenness on the surface of the target object W is inspected and under the condition of illumination by oblique incidence by the second illuminating part 2B when the inspection is for the presence or absence of defective colors, the image by diffused reflected light within the generated image being processed.

Images by regularly reflected light need not be obtained by coaxial falling illumination. For example, the half-mirror 20 may be removed and the first illuminating part 2A may be raised to set the direction of its optical axis so as the cross the optical axis of the camera 1 at the position of the standard image taking point P. In this situation, the orientation of the target object W must be adjusted such that regularly reflected light from the target object W will propagate along the optical axis of the camera 1, instead of adjusting the direction of the normal line VL at the representative point E to be along the optical axis of the camera 1.

Next, the inspection for defective unevenness by using an image of regularly reflected light will be explained.

FIG. 5 shows in correlation a sectional view of the target object seen across a line (I-I) passing through a defective indentation 40 within the target image-taking area and an image 50 obtained of the target image-taking area.

If the surface of the target object within the target image-taking area is nearly flat, as shown in FIG. 5, regularly reflected light of the coaxially falling illumination as explained above propagates opposite to the incident light, or along the optical axis of the camera 1, everywhere within the target area. In other words, a sufficient quantity of reflected light is received by the lens of the camera 1. Reflected light from the defective indentation 40, however, propagates in directions other than that of the optical axis of the camera 1. As a result, this shows as a darker area 51 than its surrounding. Thus, such a defect can be detected by binarizing the image by using a suitable threshold value.

If the surface curvature of the target object within the target image-taking area is large, however, there may appear places within the target image-taking area where regularly reflected light cannot be made incident to the lens of the camera 1. FIGS. 6A, 6B and 6C show an example of a target object with a large surface curvature and reflected light from the representative point E and two neighboring points F1 and F2 separated from the representative point E by specified distances, reaching and not reaching the lens 11 of the camera 1. Dotted lines in each of these figures indicate the range of light irradiating the corresponding point on the target surface and shaded areas indicate the ranges of reflected light. Thus, in this example, regularly reflected light from the representative point E is entirely received by the lens 11 but regularly reflected light from point F1 somewhat separated therefrom is only partially received by the lens 11. Regularly reflected light from point F2 farther separated from the representative point E is not received by the lens 11 at all. At such points from which regularly reflected light is not received by the lens, although within the target image-taking area, presence or absence of a surface defect cannot be detected by regularly reflected light.

Figure 7:
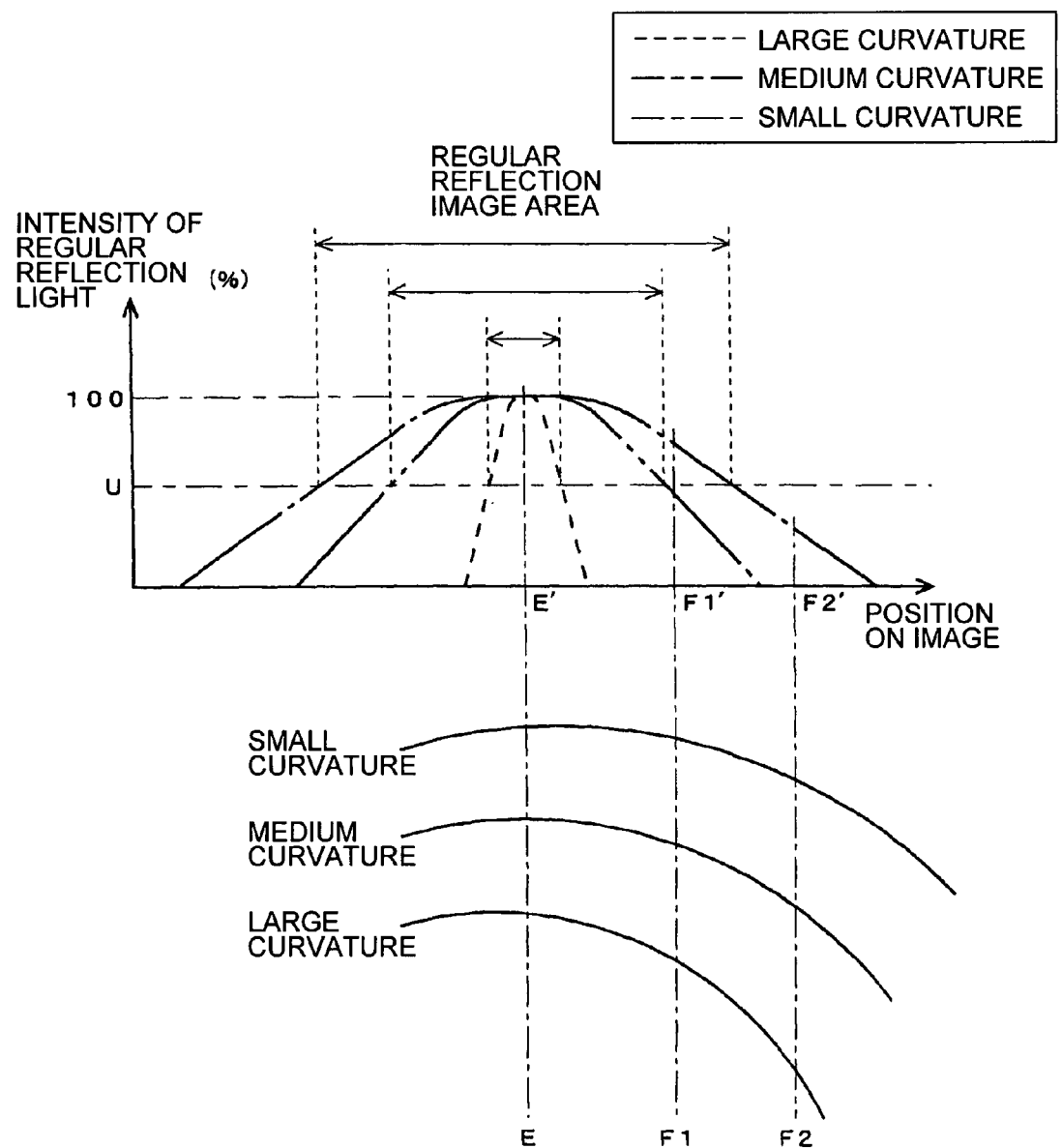
FIG. 7 is a drawing for explaining the relationship between curvature and "regular reflection image area."

The portion of the surface of the target object within the target image-taking area capable of causing the regularly reflected light therefrom to be received by the lens 11 becomes smaller as the curvature of the surface increases. This is illustrated in FIG. 7, showing three surfaces which are different in curvature, as well as the intensity distribution of regularly reflected light on the image of each generated by matching the representative point E specified on the surface of the target object with the standard image taking point P and arranging the direction of the normal line at the representative point E to coincide with the optical axis of the lens 11 of the camera 1. Each distribution curve is approximately of the shape of a parabola with the center at a point E' corresponding to the representative point E but the width of the hill-shape of the curve becomes narrower as the curvature of the surface of the target object becomes larger.

The distribution curves of FIG. 7 are normalized to 100% at point E'. On the assumption that there be no defects on the target object within the target image-taking area, the area wherein the intensity of the reflected light becomes greater than a specified percentage U is referred to as "regular reflection image area", or the area wherein an image by regularly reflected light can appear. The boundary of the regular reflection image area may be defined where the intensity of the regularly reflected light becomes zero but it is preferable to define the boundary based on a threshold value as in the illustrated example in order to secure the accuracy of inspection.

As will be explained below with reference to FIG. 9, the intensity distribution of regularly reflected light may be sometimes superposed with reflected light as noise components caused by small protrusions and indentations on the surface of the target object other than the defects. If the threshold value U is made too small, the boundary of the regular reflection image area tends to become unstable due to these noise components. It is therefore important to set the target inspection area such that portions close to the boundary of this area will not be included in the regular reflection image area. The target area of inspection need not be somewhat smaller than and of the same shape as the regular reflection image area but may be of any shape such as a rectangular shape. When the threshold value U is set to be somewhat large or the noise components are few, the whole of the regular reflection image area may be defined as the target inspection area. In such a case, the target inspection area need not be defined separately from the regular reflection image area.

In order to inspect every target surface portion of inspection of the target object, images are taken of the target object while its position and orientation are varied. The position and orientation of the target object are set such that every portion (or every position and every surface point) to be inspected should appear within the target inspection area of at least one of the images that are taken. The setting of the position and orientation of the target object, however, is not effected by using data that directly represent the position and orientation of the target object in the stu-coordinate space as shown in FIG. 2 or data (such as the rotary angles of the six shafts) that show the position of the robot 3 supporting the target object. Instead, use is made, according to the present example, of data that indirectly represent the position and orientation of the target object, or the x, y and z coordinates of the representative point E as the directional angles α and β of the normal line VL shown in FIG. 3 with reference to the target object. These data are converted by the robot controller 4 into data for determining the operations of the robot 3.

As the position and orientation of the target object W are thus determined by the set data, the target image-taking areas on the target object W are accordingly determined.

Figure 8:
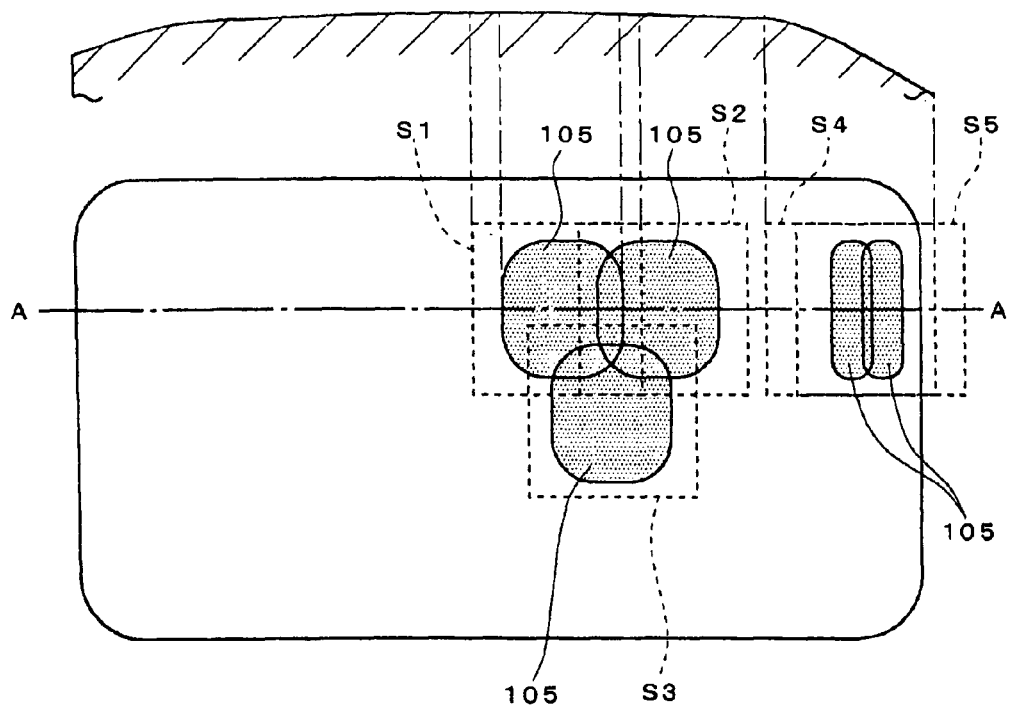
FIG. 8 is a drawing for showing examples of target area set for inspection on a target object.

FIG. 8 shows examples of target image-taking areas S1, S2, S3, S4 and S5 for inspection on a target object W, including both its plan view as seen from above and its sectional view taken along line A-A. The areas on the target object corresponding to the target inspection areas on the images generated individually for the target image-taking areas S1-S5 are shown in FIG. 8 as shaded areas 105 (hereinafter referred to as "assigned areas" 105). Although the target image-taking areas S1-S5 shown in FIG. 8 are all rectangular and of the same size and distributed along the surface of the paper, it is for the convenience of description and they may be of any complicated shape because they correspond to areas on the target object W of which images are taken from various directions for obtaining images of regularly reflected light from all places on the target surface for inspection. Target areas S4 and S5 have portions that are not on the target object W but from the definition of the target surface, these portions are not considered to be a part of a target image-taking area.

In order not to miss any point for inspection, it is advisable to set the position and orientation of the target object W such that assigned areas 105 overlap mutually, as shown in FIG. 8.

At places where the curvature of the surface of the target object W is small (or the curving is gentle), the area of image by regularly reflected light is large, as explained above, and hence the corresponding target inspection area on the image can be relatively large. Accordingly, corresponding assigned areas 105 can be relatively large. On the other hand, areas of image by regularly reflected light become small at places where the curvature of the surface of the target object W is large (or the curving is sharp) and hence large target inspection areas cannot be set and hence the corresponding assigned areas 105 become small. Thus, target image-taking areas (such as S4 and S5) where the surface curvature is large must be distributed more densely than target image-taking areas (such as S1, S2 and S3) where the surface curvature is small (or the curving is gentle).

According to the present example, an image of an object considered to have no defect (hereinafter referred to as a model object W0) is used to carry out a differential calculation process with an image of the target object W, and the differential image generated by this calculation is binalized to detect a defect.

Figure 9A:
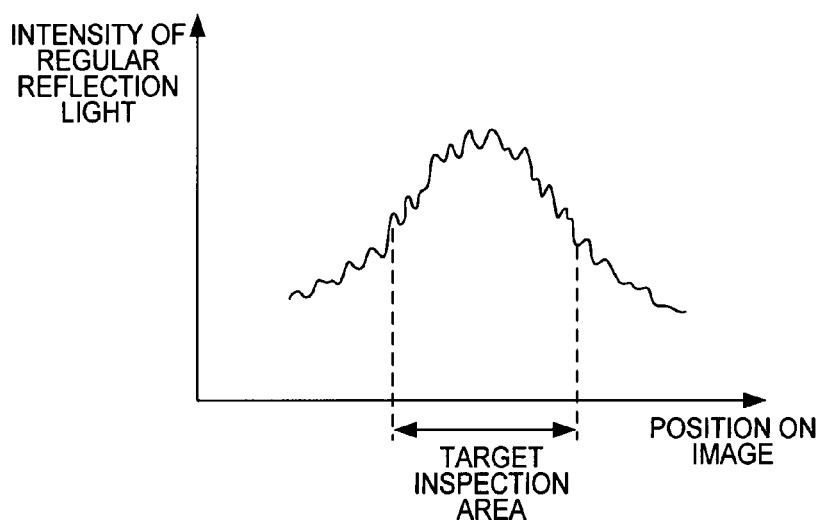
FIGS. 9A, 9B and 9C are graphs for explaining a method of detecting defects.
Figure 9B:
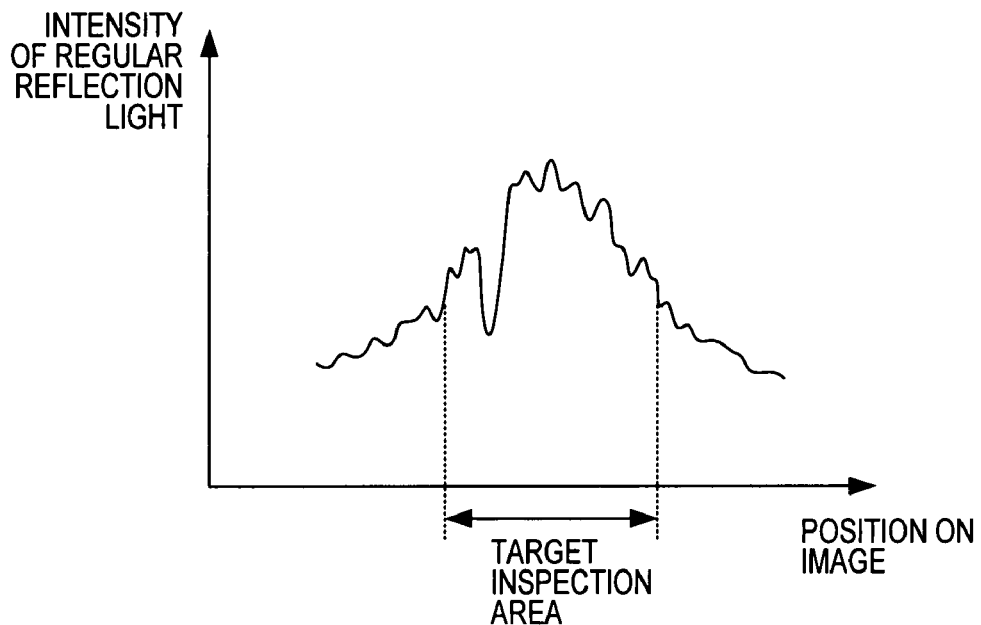
Figure 9C:
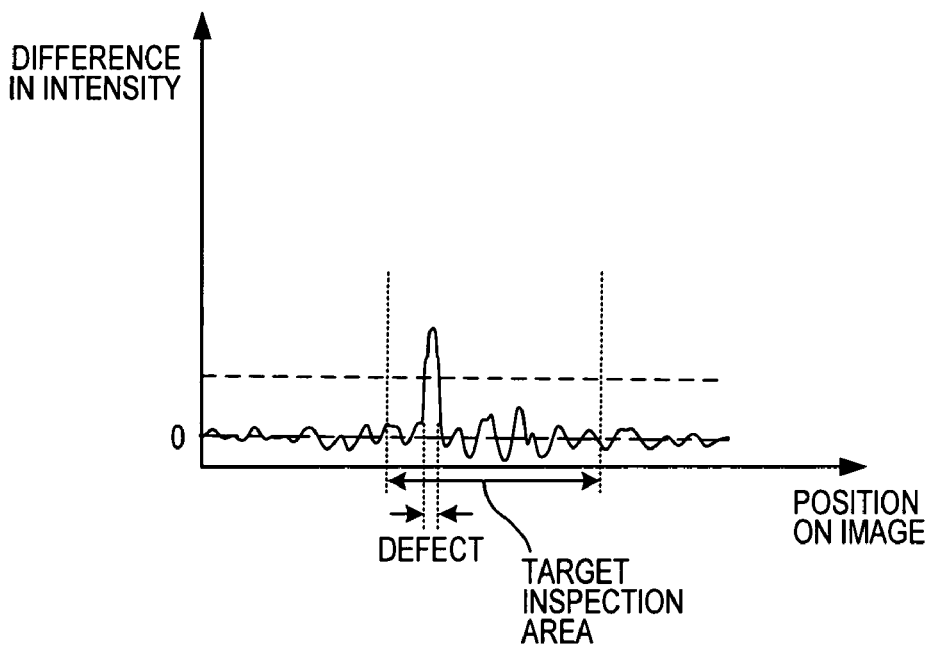

FIGS. 9A, 9B and 9C are referenced next to explain a method of detecting defects on a target area. FIG. 9A shows a distribution of intensity on an image by regularly reflected light from an image obtained from a model object W0, and FIG. 9B shows a distribution of intensity on an image by regularly reflected light from an image obtained from a target object W with defective unevenness. It is to be noted that these distribution curves show small variations due to superposition of noise components. FIG. 9C shows the intensity distribution of the differential image generated from the two aforementioned images by taking differentials of individual pixels, or what is obtained by subtracting the intensity distribution of FIG. 9B from that of FIG. 9A. The intensity distribution of this differential image is binalized and the portions where an intensity differential exceeding a threshold value are recognized as defects.

In the above, the threshold value is determined not only by the overall intensity distribution of the image by regularly reflected light on the image (such as whether the light intensity is large or small as a whole) but also by considering the magnitude of the noise components superposed to the intensity distribution of the image by regularly reflected light. These noise components are generated by the small unevenness of the surface which is not large enough to be considered a defect. Thus, the threshold value for the binarization must be determined to be larger than the size of the noise components that appear in the intensity differential of the image by regularly reflected light.

Figure 10:
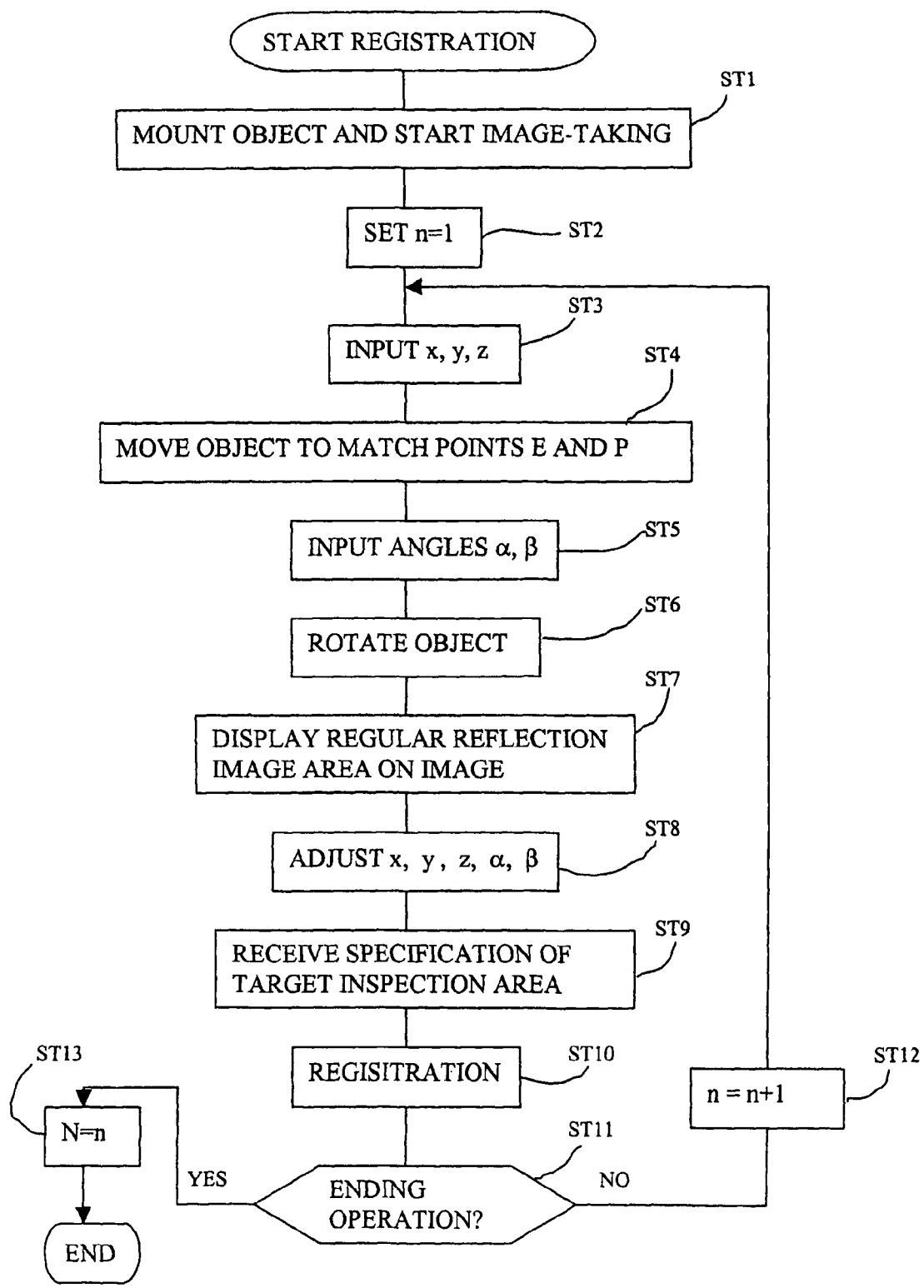
FIG. 10 is a flowchart of the processes for registering the position and orientation of a target object and data for setting target areas.

Next, an example of pre-inspection preparation is explained. Firstly, the position and orientation of the target object W at the time of inspection, data for setting target inspection areas and the binarization threshold value for the image processing for the detection of defects are determined in the pre-inspection preparation mode and registered in a memory (not shown) of the process control device 6. FIG. 10 shows the flow of processes in the aforementioned preparation mode for registering data for setting the position of the target object W at the time of the inspection (such as the x-, y- and z-coordinates of the representative point E), data for setting the orientation of the target object W (such as directional angles $\alpha$ and $\beta$ of the normal line VL at the representative point E) and data for setting target inspection areas (such as image data painting the target inspection areas and other areas differently or data indicative of the boundary lines of the target inspection areas).

These processes are carried out by using a model object W0 while input operations by the user and the input of parameters are being received. It is mainly the process control device 6 that carries out the processes but all components shown in FIG. 1 participate.

In this registration process according to the present example, the camera 1 is operated continuously and the input by the user is received while the generated images are displayed on the monitor 8. After the model object W0 is mounted to the end arm 35 of the robot 3 and the image-taking process by the camera 1 is started (Step ST1), the ID number n of the target image-taking area (hereinafter referred to as the image number n) is set to its initial value 1 (Step ST2).

Next, the user's input of the x-, y- and z-coordinates is received (Step ST3) and the robot 3 is moved according to the inputted coordinates such that the model object W0 is moved and the representative point E comes to the position of the standard image taking point P (Step ST4).

Next the input of the directional angles $\alpha$ and $\beta$ at the representative point E is received (Step ST6) and the robot 3 is moved to adjust the orientation of the model object W0 such that the direction of the normal line VL shown by the directional angles $\alpha$ and $\beta$ will match the optical axis of the camera 1.

Figure 11A:
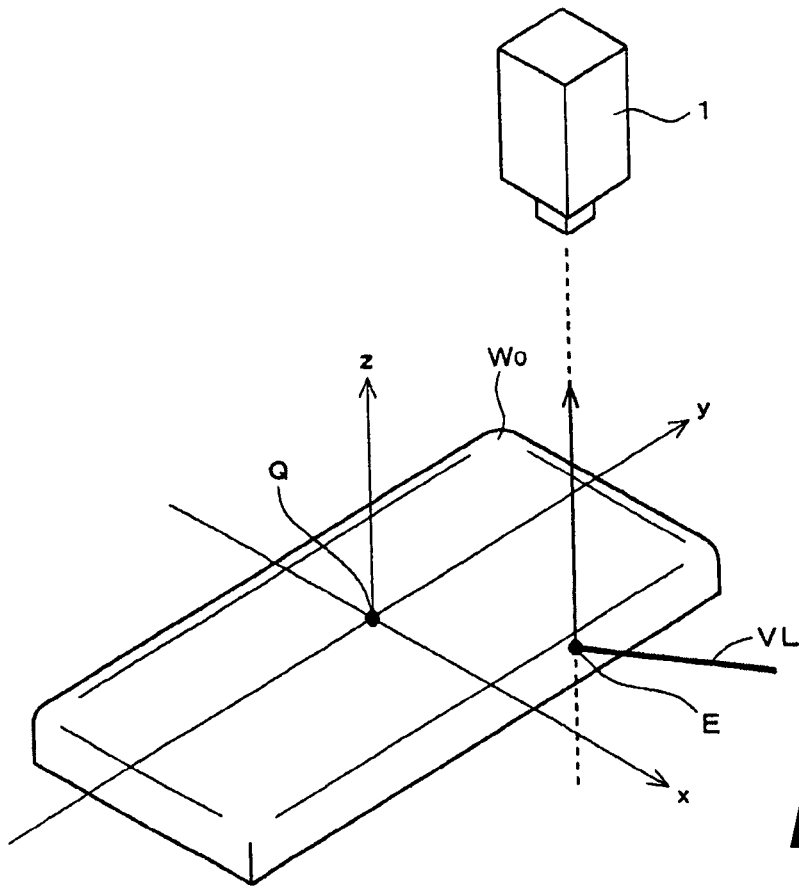
FIGS. 11A and 11B show the changes in the orientation of the object in Steps ST4-ST6 of FIG. 10.
Figure 11B:
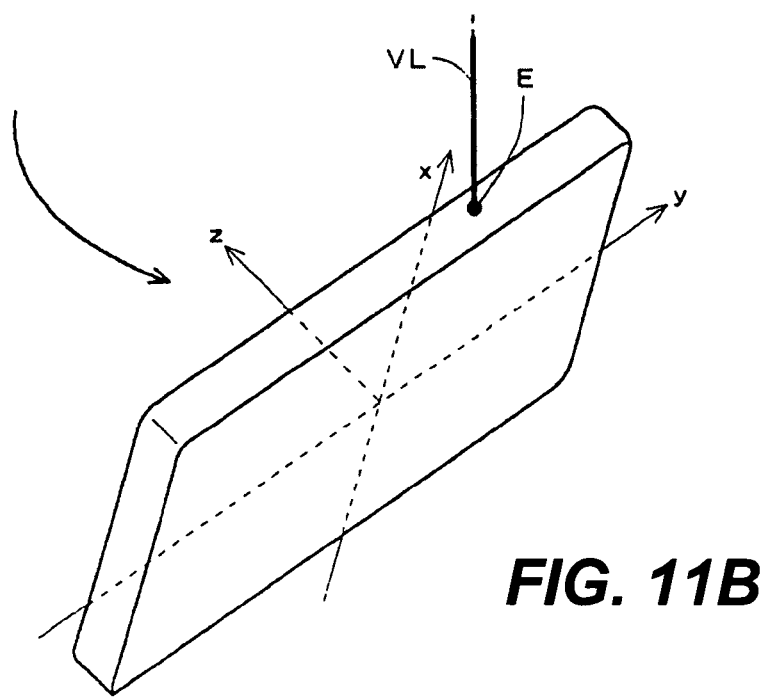

FIGS. 11A and 11B show the changes in the orientation of the model object W0 in Steps ST4-ST6. As Step ST4 is carried out, the representative point E comes to the position of the standard image taking point P as shown in FIG. 11A but since the orientation prior to this position-matching is still maintained, the z-axis is parallel to the optical axis of the camera 1 at this time. After Steps ST5 and ST6 are carried out, the model object W0 is rotated such that the normal line VL at the representative point E comes to be in the direction of the optical axis of the camera 1. In these processes, it may be sufficient to input only approximate numbers for the directional angles $\alpha$ and $\beta$. When the coordinates are inputted in Step ST3 by using a plan view of the model object W0, it may be sufficient to input only the x- and y-coordinates, the user adjusting the z-coordinate later while watching the monitor 8 for focusing.

Next, with reference back to FIG. 10, an image is taken of the model object W0 while coaxial falling illumination is effected thereon by the first illuminating part 2A (Step ST7). An image thus generated is displayed on the monitor 8 and a threshold value U is used to extract a regular reflection image area and the range of this area is discriminatingly displayed on the same image. This discriminating display may be effected by completely filling the area or by showing its boundary line.

Next, the values of x, y, z, $\alpha$ and $\beta$ are adjusted such that the regular reflection image area will come to the center of the entire image, if necessary (Step ST8). In this step, processes similar to Steps ST3-ST7 may be repeated any number of times. Next, the user's operation for specifying a target inspection area for inspection is accepted (Step ST9). The target inspection area can be specified only within the range of the regular reflection image area. Step ST9 may be omitted if the regular reflection image area itself is to be the target inspection area.

Next, the x-, y- and z-coordinates of the representative point E and the directional angles $\alpha$ and $\beta$ are registered in a memory in correlation with the image number n (Step ST10). The position and size of the area on the image corresponding to the target inspection area specified in Step ST9 are also registered as set data in correlation with the image number n.

Next, the image number n is incremented by 1 (Step ST12) until an ending operation is carried out and the processes of Steps ST3-ST10 are repeated.

The processes of Steps ST3-ST11 are together referred to as the "first setting unit process". In Step ST4 in the second cycle and thereafter, a new representative point E is brought onto the optical axis of the camera 1 in principle by maintaining the direction adjusted to the optical axis of the camera 1 in the previous step. If there is a big change in direction, however, the position-matching operation may be carried out after returning once to the initial condition where the z-axis is matched to the optical axis.

As Steps ST3-ST10 are repeated, not only do a plurality of target image-taking areas come to be sequentially set on the target surface of the model object W0, but also the set data on its position and orientation (the coordinates of the representative point E and angles $\alpha$ and $\beta$) and set data of the target inspection areas on the image corresponding to that area are registered.

As the ending operation is carried out (YES in Step ST11), the value of the image number n at that time is registered as the total image number N and the process ends.

In this registration process described above, it is necessary for the user to ascertain that all positions of the target inspection surface are included in the assigned area. This may be done, for example, by preliminarily marking the target inspection surface of the model object so as to partition it into a plurality of areas (say, by drawing boundary lines between the areas and writing in a number for each area) and recording assigned areas on a separated prepared map of the target inspection surface while observing the markings appearing within the inspection target areas on the image.

Alternatively, a plane with its normal line in the direction shown by angles $\alpha$ and $\beta$ may be set, every time a target inspection area is set, as a plane approximating a curved surface included in the target inspection area on the model object W0, and a synthesized image may be displayed such that the group of these approximating planes appears to be three-dimensionally superposed to the image of the model object W0. If the group of these approximating planes is displayed so as to move in correlation with the changes in the position and direction of the model object W0, parts contained in the assigned areas can be acknowledged without marking the actual model object W0.

For optimizing the distribution of the target inspection areas, a portion of the set data once registered by the process of FIG. 10 may be corrected while the model object W0 is supported again by the robot 3 and images are obtained by the camera 1.

Although FIG. 10 shows an example wherein a series of processes is carried out based on the user's operations, all or a part of the processes (Steps ST3, ST5 and ST11) operated by the user may be carried out as program processing by a computer.

Figure 12:
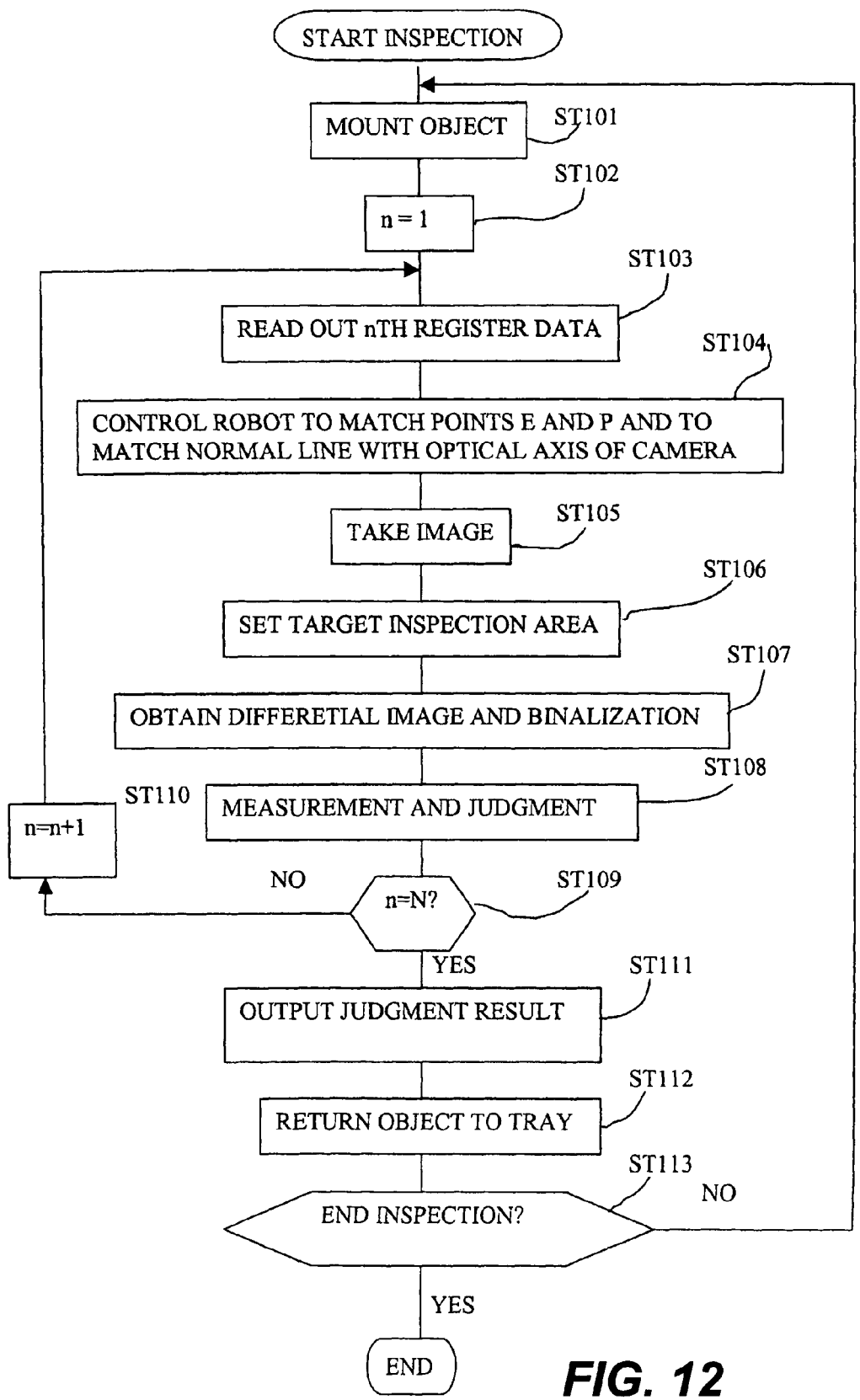
FIG. 12 is a flowchart of the inspection process.

FIG. 12 shows a flow of processes for an inspection, or a routine for sequentially inspecting a plurality of target objects W contained in the tray 36. Firstly, the robot 3 is operated to mount the first target object W onto the end arm 35 (Step ST101) and the image number n is initialized to 1 (Step ST102). Next, the nth registered data items are read out (Step ST103) and the motion of the robot 3 is controlled such that the representative point E will match the standard image taking point P based on the x-, y- and z-coordinates within the nth data items and the direction of the normal line VL at the representative point E will coincide with the optical axis of the camera 1 based on the angles α and β in the aforementioned registered data (Step ST104).

After an image is taken next while this orientation is maintained (Step ST105), target inspection areas are set on the image thus generated on the basis of set data in the aforementioned registered data (Step ST106). Next, images in these target inspection areas are cut out and a differential image with the image of the model object W0 by the method explained above with reference to FIG. 9 and this differential image is binalized (Step ST107). A measurement process including counting the number of pixels exceeding a threshold value is carried out on the binalized image and this measured value is compared with a specified reference value to judge whether the target inspection areas on the target object W are good or defective (Step ST108).

After the image number n is incremented by 1 (Step ST110), the routine returns to Step ST103 and Steps ST103-ST108 are repeated until the image number n reaches the total image number N (YES in Step ST109), taking images of the target image-taking areas and inspecting them by using images by regularly reflected light.

After all target image-taking areas have been processed (YES in Step ST109), inspection result data are created by combining the results of judgments for all image numbers and outputted to the monitor 8 or an external apparatus (not shown) (Step ST111). Thereafter, the robot 3 is activated again to return the target object W back to the tray 36 (Step ST112). If there is still a target object not processed yet (NO in Step ST 113), the routine returns to Step ST 101. If Steps ST101-ST112 are carried out on all of the target objects W (Yes in Step ST113), the inspection process ends.

By a process described above, the presence and absence of defective unevenness can be accurately detected over the whole target surface of inspection since it is set on the basis of the data set in the preparation mode such that every place on the target inspection surface of the target object will appear in at a target inspection area on at least one of the images that are taken.

Although it was explained above that a differential calculation is carried out between an image within the target inspection area with the image of the model object W0, a differential image may be obtained by using the image taken at the time of inspection and the entire area of the image of the model object W0 without distinguishing between inside and outside the target inspection area. Even in this case, it may be expected that defects exceeding a threshold value would be detected on the differential image mostly within the target inspection area where the light intensity is high. There may be situations wherein defects are detected outside the target inspection area but such defects will probably be detected doubly also from an image of an neighboring area on the target object W.

The inspection is not limited to methods using a differential image as explained above. Many known methods may be used for the purpose of this invention such as the method of detecting a place where the image density changes suddenly as a defect or the method of detecting and classifying defects by using a knowledge on characteristics on the image corresponding to the kinds of defects (such as the area and shape of the defect).

In the registration process shown in FIG. 10, set data on the position and orientation of the target object W and target inspection areas are set while images of the model object W0 are actually obtained. It is possible, however, to set each condition automatically or semi-automatically by using three-dimensional data of the target object W such as CAD data and without activating the robot 3. Next, this automatic setting process will be explained.

Figure 13A:
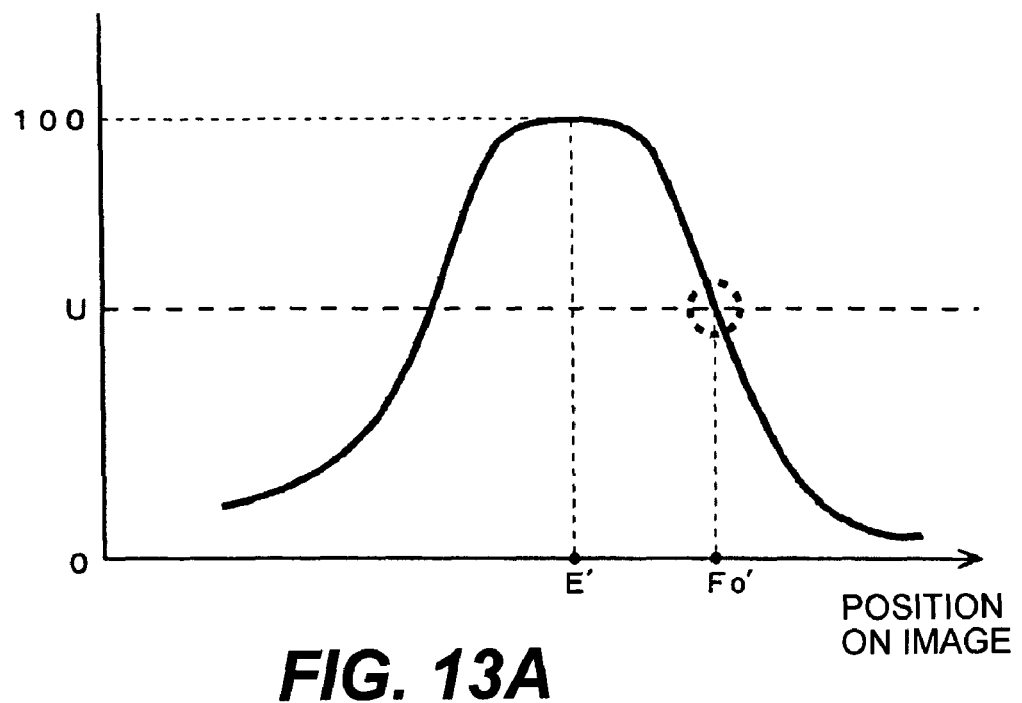
FIG. 13A is a graph showing the intensity distribution of the regularly reflected light on the image.
Figure 13B:
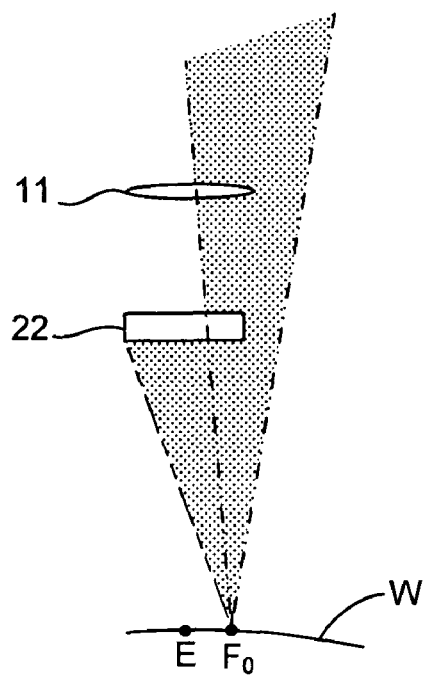
FIG. 13B shows the light irradiating the target object and its relationship with the regularly reflected light the optical system.

FIG. 13A shows the intensity distribution of the regularly reflected light on the aforementioned image, and FIG. 13B shows the light irradiating the target object W and its relationship with the regularly reflected light and the optical system. FIG. 13B neglects the bending of optical path due to the half-mirror 20. FIG. 13A shows the intensity distribution along one line on the image by defining 100% to be the intensity at point E' corresponding to the representative point E.

In what follows, it will be assumed that regularly reflected light from the representative point E on the target object W is incident on the entire surface of the lens 11 of the camera 1. On this premise, the threshold value for identifying the aforementioned regular reflection image area may be replaced by the ratio of the incident area of regularly reflected light on the lens 11 with respect to the entire area of the lens 11. In other words, if the ratio of the intensity of regularly reflected light at point F0' at the boundary position of the regular reflection image area in the graph of FIG. 13A with respect to the intensity at point E' is U(%), the ratio of the area on which regularly reflected light from point F0 on the target object W corresponding to point F0' with respect to the entire area of the lens 11 of the camera 1 will be U(%).

Figure 14:
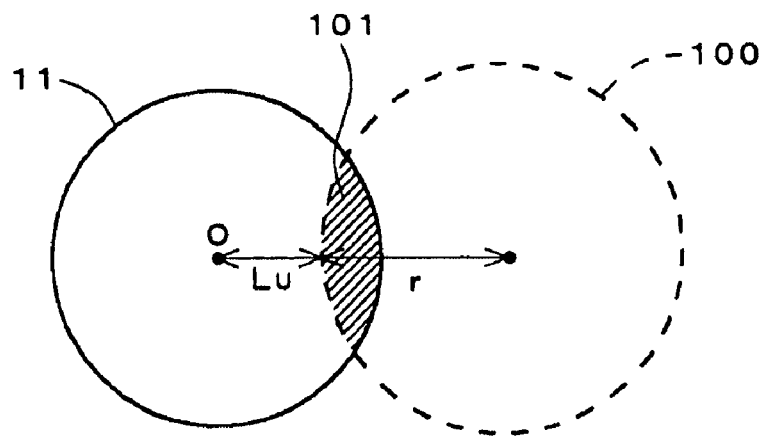
FIG. 14 is a drawing for showing the relationship between the lens and regularly reflected light.

FIG. 14 shows the relationship between regularly reflected light from point F0 and the lens 11 of the camera 1, as seen from above the lens 11. In this figure, the dotted circle 100 indicates the regularly reflected light at the height of the lens 11 and r indicates its radius. The shaded area 101 indicates the area on which the regularly reflected light is incident (hereinafter referred to as the "regular reflection light incident area 101").

With reference to FIG. 14, the distance Lu from the center O of the lens 11 to the boundary of the regular reflection light incident area 101 can be obtained from the area of this area

101 and radius r. As for the length of radius r, this can be obtained as explained below with reference to FIG. 15.

Figure 15:
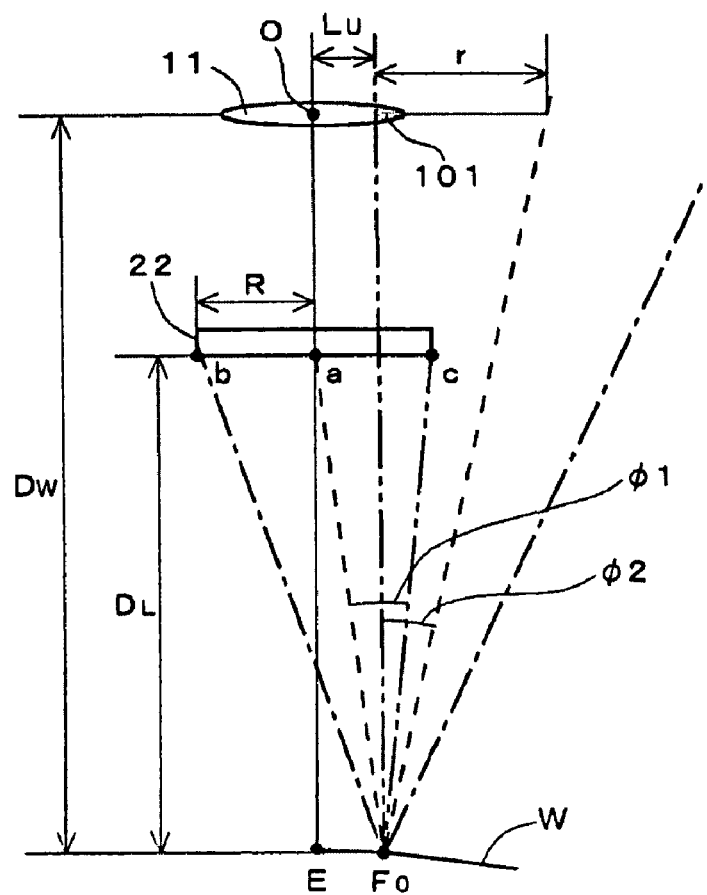
FIGS. 15 and 16 are drawings for explaining the principle of obtaining the radius of regularly reflected light.

In FIG. 15, DL indicates the distance from point F0 to the light-projecting surface of the illuminating parts 2A (or the front surface of the diffusing plate 22), DW indicates the distance from point F0 to the lens 11 and R indicates the aforementioned light-projecting surface. FIG. 15 shows the ranges of the illuminating light and the reflecting light to and from point F0. Broken lines in FIG. 15 indicate light from the center a of the light-projecting surface and its regular reflection. One-dot chain lines indicate light from an edge point b of the light-projecting surface and regularly reflected light corresponding to it. Two-dot chain lines indicate light from another edge point c opposite from edge point b with respect to the center a and regularly reflected light corresponding to it. In this example, the regularly reflected light corresponding to the projected light from point c determines the boundary of the regular reflection light incident area 101.

In this example, the angle between the illuminating light to point F0 and its regularly reflected light is bisected by the normal line at point F0. Since this is true regarding illuminating light from points a and c, angle $\Phi 1$ between illuminating light from point a and illuminating light from c is equal to angle $\Phi 2$ between their regularly reflected lights. Thus, radius r can be obtained as $$r = (R \cdot DW)/DL. \quad \text{Formula (1)}$$

In other words, since radius r of the regularly reflected light 100 can be obtained from known values R, DW and DL, this value and the area of the regular reflection light incident area 101 may be used to obtain the value of distance Lu.

Although it was assumed in the explanation given above that regularly reflected light from the representative point E enters the entire surface of the lens 11, if this is not the case, distance Lu for which the area of the regular reflection light incident area 101 would be U(%) may be obtained, the portion of the area of the lens 11 onto which regularly reflected light from the representative point E being counted as 100%.

Next, the distance of separation between the representative point E and point F0 on the target object W satisfying the condition that U % of regularly reflected light incident from the representative point E to the lens 11 makes incidence.

Figure 16:
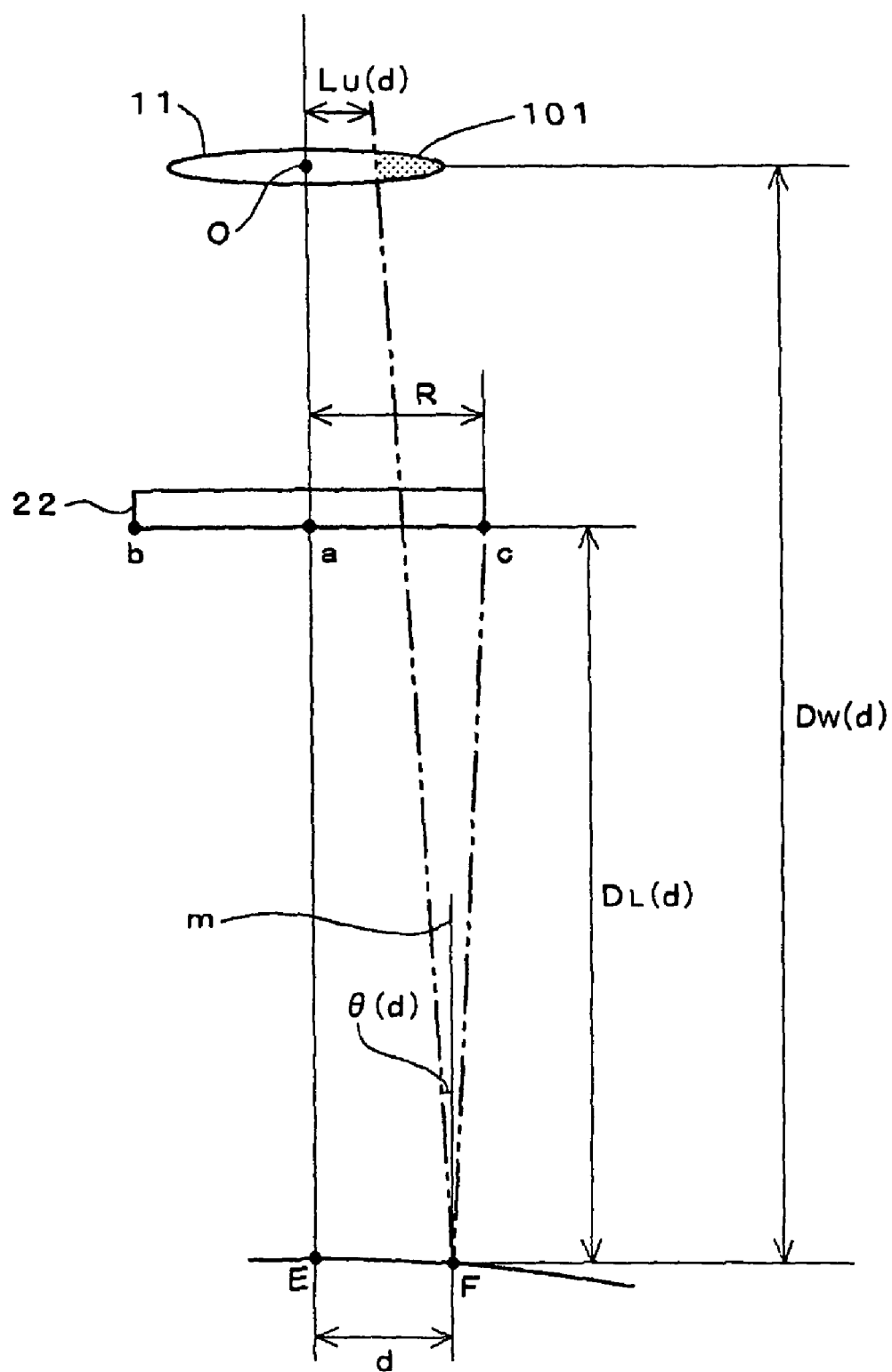

FIG. 16 shows the relationship regarding an arbitrarily selected point F on the target object between the regularly reflected light for determining the regular reflection light incident area (the regularly reflected light corresponding to point "c" on the light-projecting surface) and the optical system. The distance between the representative point E and the selected point F is shows as d, and parameters corresponding to distances Lu, DW and DL may be written as Lu(d), DW(d) and DL(d) because they are functions of d.

Next, a straight line m is drawn parallel to the optical axis of the camera 1 with F as its starting point, and if the angle in the counter-clockwise direction from line m to the regularly reflected light to point c on the light-projecting surface is defined as $\theta(d)$, Lu(d) can be expressed as follows:

$$Lu(d) = d - DW(d)\tan \theta(d). \quad \text{Formula (2)}$$

In the above, angle $\theta(d)$ can be obtained from the slope of the tangent plane at F, the radium R of the light-projecting surface and distance DL(d) from point F to the light-projecting surface. Radius R is known and distance DL(d) can be obtained from the three-dimensional coordinates of point F shown by the aforementioned three-dimensional data. The slope of the tangent plane at point F can also be obtained from the curvature data and functions indicating slopes included in the three-dimensional data. Thus, a specific value of angle $\theta(d)$ can be obtained if distance d is given. Distance DW(d) can also be determined similarly as DL(d). Alternatively, DW(d) and DL(d) may be each considered to be approximately equal to a constant, and such approximately equal constants may be used in calculating Formulas (1) and (2). In summary, the value of Lu(d) can be obtained for a given value of d.

If point F is closer to the representative point E than point F0, the regular reflection light incident area 101 corresponding to point F should be larger than that corresponding to point F0. Thus, Lu(d)≦Lu if one considers to the extent where point F matched point F0.

Thus, if the range of d is extracted wherein the value of Lu(d) obtained from Formula (2) becomes equal to or smaller than Lu, the area (hereinafter referred to as the "assignment candidate area") on the target object W corresponding to the aforementioned regular reflection image area can be obtained.

Figure 17:
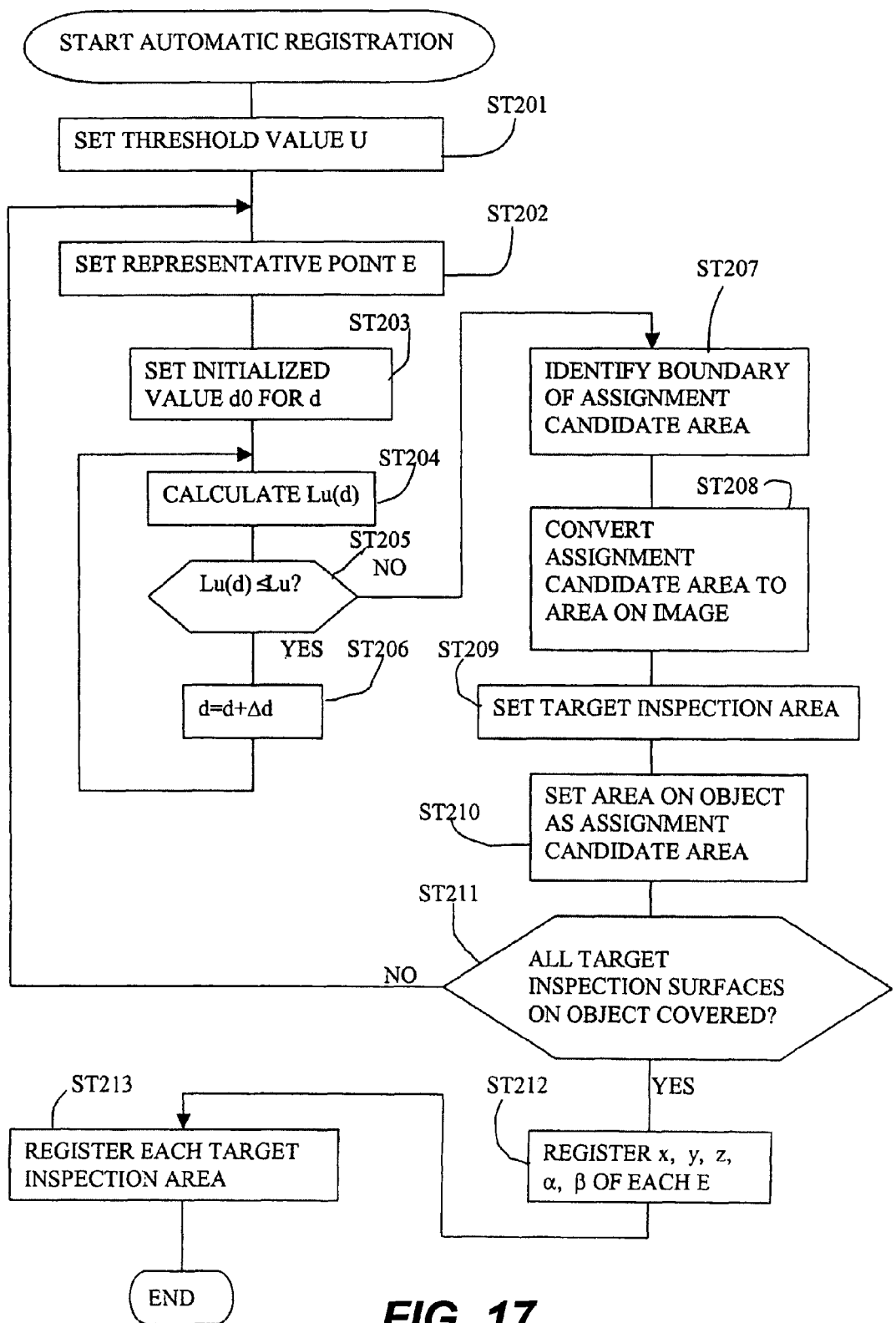
FIG. 17 is a flowchart of process steps for automatically setting image-taking conditions and data for target inspection area by using CAD data.

FIG. 17 shows the flow of process steps for automatically setting image-taking conditions and set data for target inspection area by using CAD data. After the user's input of a value of U for determining the threshold value is received (Step ST201), one of the points on the target inspection surface represented by the CAD data is selected as the representative point E and the direction of the normal line at this point is calculated (Step ST202).

Next, an initial value d$\theta$ (such as $\Delta$d>0) for distance d is set (Step ST203). The CAD data are used to obtain values of DW(d) and tan $\theta$(d), and these values are used in Formula (2) to calculate Lu(d) (Step ST204). This value is then compared with the value Lu which is preliminarily obtained by using Formula (1). If Lu(d)≦Lu (YES in Step ST205), the value of d is incremented by $\Delta$d (Step ST206) and the routine returns to Step ST204 for repeating Steps ST204 and ST205 until Lu(d) becomes greater than Lu (NO in Step ST205) and the routine goes out of the loop.

As Lu(d) becomes greater than Lu, the x-, y- and z-coordinates of the representative point E and the previous value of d (that is, d−$\Delta$d) are used for obtaining the coordinates of the boundary of the assignment candidate area (Step ST207).

Strictly speaking, only one point on the boundary of the assignment candidate area is determined by Steps ST204-ST206. If the surface area near the representative point E can be approximated by a spherical surface, however, such spherical surface may be set as the assignment candidate area. If the curvature of the surrounding surface areas of the representative point E varies, depending on the direction, the direction corresponding to the maximum curvature and the direction corresponding to the minimum curvature are determined and Steps ST204-ST206 are repeated for each of these directions. In such a situation, an elliptical area having major and minor axes in these two directions is set inside the target image-taking area as the assignment candidate area. If the shape of the surrounding area of the representative point E is complicated, Steps ST4-ST6 are carried out in more directions to set the assignment candidate area by using the values of d obtained in these direction.

After the assignment candidate area is determined, it is converted into an area on the image obtained by the camera 1 from this assignment candidate area on the target object (Step ST208). In the above, it is premised that the representative point E is matched to the standard image taking point P and the direction of the normal line at the representative point E coincides with the optical axis of the camera 1 such that the area on the image obtained by this conversion corresponds to the regular reflection image area.

Next, a rectangular area of a specified size included in the aforementioned regular reflection image area is set as the target inspection area (Step ST209). Alternatively, the regular reflection image area may be directly set to be the target inspection area. Next, an area on the target object corresponding to the target inspection area on the image is obtained by a conversion which is inverse to the process step in Step ST208 (Step ST210) and is set as the assigned area.

Thereafter, Steps ST202-ST210 are repeated until the whole of the target inspection surface becomes covered with assigned areas. The processes of Steps ST202-ST210 are together referred to as the "second setting unit process".

As the target inspection surface is thus completely covered (YES in Step ST211), the s-, y- and z-coordinates of the representative point E which is selected each time and angles α and β are registered as parameters for determining the position and orientation of the target object W (Step ST212). Each target inspection area corresponding to each representative point E is also registered (Step ST213). These data registered in Steps ST212 and ST213 are correlated to the image number n, as shown in FIG. 10.

As for the selection of representative points E, this may be done by preliminarily partitioning the target object W into areas within each of which the curvature is similar, based on the CAD data, and selecting a number of points for each of the partitioned areas corresponding to the area and orientation of the area. In this case, too, it is necessary to adjust the intervals between the representative points E as shown in FIG. 8 according to the curvature such that the target image-taking areas will be dense where the curvature is large. In spite of this, it is desirable to make the intervals between the representative points E as large as possible within the limit such that no inspection points will be missed. This is in order to reduce the number of times of taking images such that the time required for moving the robot 3 and sequentially adjusting the position and orientation of the target object can be reduced and hence the time required for the inspection can be shortened. The position of each representative point E may be adapted to be inputted by the user.

Although FIG. 17 shows a routine wherein the loop of Steps ST202-ST211 is repeated until the target inspection positions are completely covered by the assigned areas, the number of cycles for repeating the loop may be preliminarily fixed, it being judged whether the target inspection surface has been completely covered or not when the fixed number of cycles have been repeated and the processes being repeated from the beginning if not covered. In such a case, the intervals between the representative points E are made relatively large but are made smaller each time the loop is repeated such that no inspection point will be missed and the inspection can be carried out efficiently.

Figure 18:
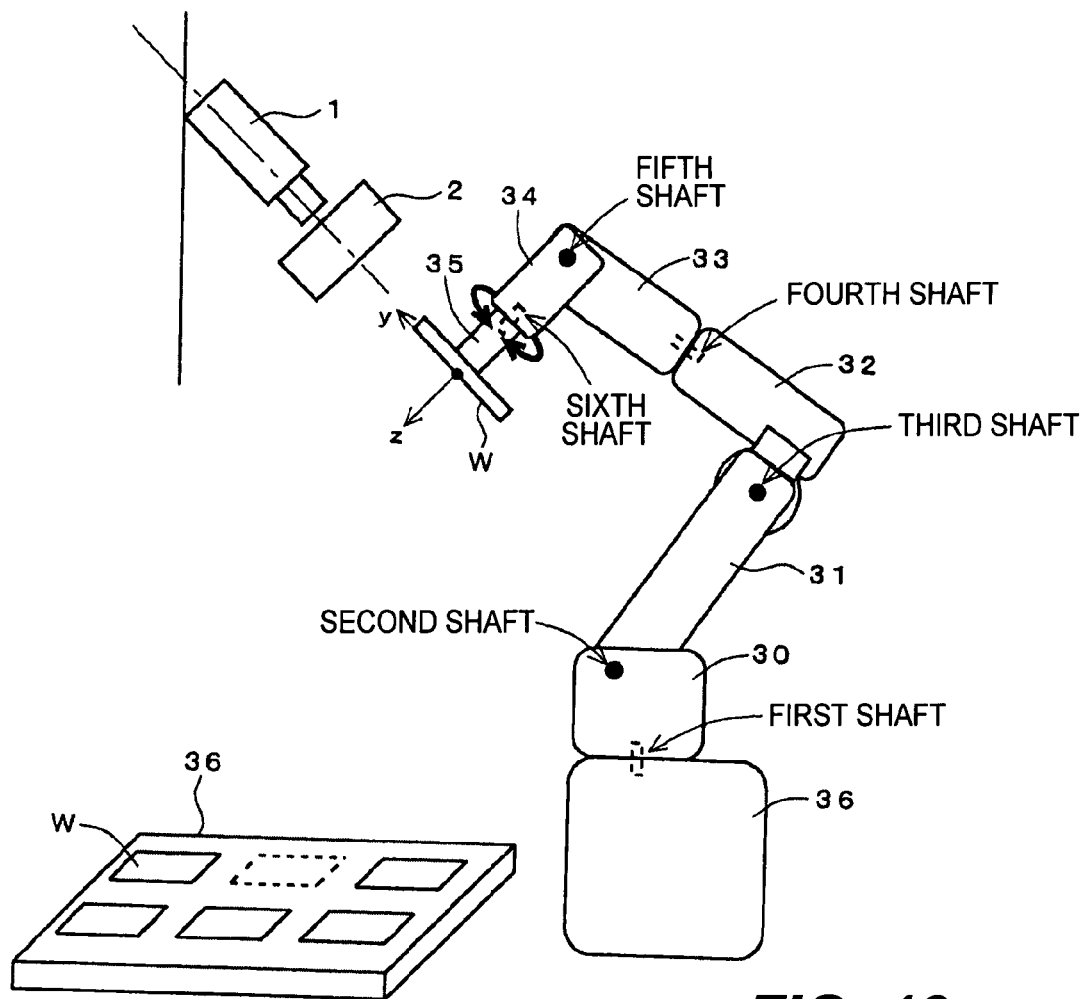
FIG. 18 is a drawing for showing the operation of the robot when a side surface of a target object is inspected.

FIG. 18 shows the operation of the robot 3 when a side surface of the target object W is inspected by the inspection device 10. In this example, the z-axis is pointed obliquely downward in a vertical plane containing the optical axis of the camera 1 such that a side surface (the surface with its normal line pointing in the +y-direction) faces the camera 1. It is principally the sixth shaft that is rotated to switch the target image-taking area. The rotary angle of the fifth shaft is adjusted according to the direction of the normal line VL at the representative point of each target image-taking area.

As the robot 3 is operated as above, images are taken of the target object W as it is rotated around the z-axis such that an approximately fixed direction of the images coincides the direction of the thickness (the z-direction) of the target object W. Thus, as the images obtained each time are displayed on the monitor 8, the user may find it difficult to immediately judge which of the side surfaces is being photographed.

In view of this potential problem, the image generated by the camera 1 is corrected according to the angle of rotation by the sixth shaft and the image thus corrected is displayed on the monitor 8. This correction process is explained next with reference to FIGS. 19 and 20.

Figure 19:
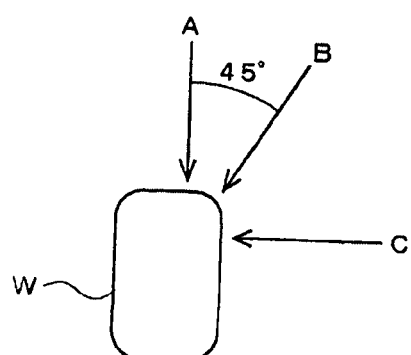
FIG. 19 is a drawing for showing the image-taking direction for the inspection of a side surface of the target object.

FIG. 19 shows three image-taking processes taken in three different directions with respect to the target object W as indicated by arrows A, B and C. For the convenience of description, the sixth shaft is rotated each time by 45°. The upward direction is FIG. 19 is the z-direction.

Figures 20A, 20B, 20C:
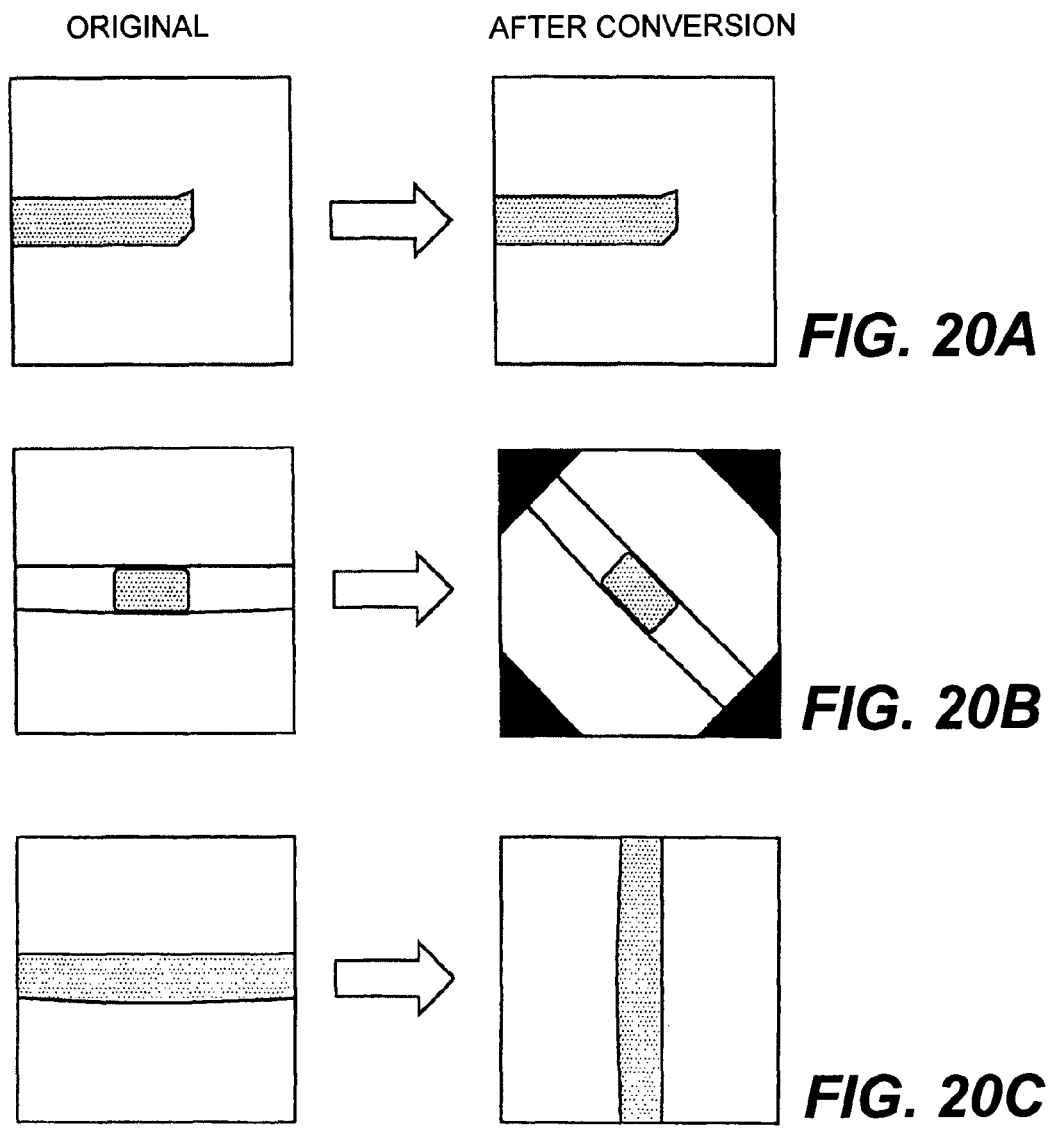
FIGS. 20A, 20B and 20C are drawings for showing the image conversion processes for each of the directions shown in FIG. 19.

FIGS. 20A, 20B and 20C each show the original image taken by the camera 1 and corresponding corrected image for the display on the monitor 8. Each shaded area indicates the regular reflection image area. The black portions in FIG. 20B are because there are no corresponding pixels on the original (before the conversion) image.

In the present example, the image taken each time is rotated in the clockwise direction by an angle corresponding to the angle of rotation of the sixth shaft at the time of taking the image. If the sixth shaft is rotated in the clockwise direction, the image must be rotated in the counter-clockwise direction.

In this example, the direction of rotation of the sixth axis is opposite to that of the correction on the image. If the initial orientation of the target object W shown in FIG. 18 is rotated by 180° in the z-direction, the direction of rotation of the sixth shaft and the direction of correction become the same.

By a correction as described above, an image similar to the situation where the target object W originally having its front surface facing the camera 1 has been rotated by a single twist such that its side surface came to face the camera 1 can be obtained. Thus, a display can be made which may be naturally expected by the user holding the target object W actually in the hand. In other words, the user can easily understand from the display on the monitor 8 which of the side surfaces is being inspected.

Figure 21:
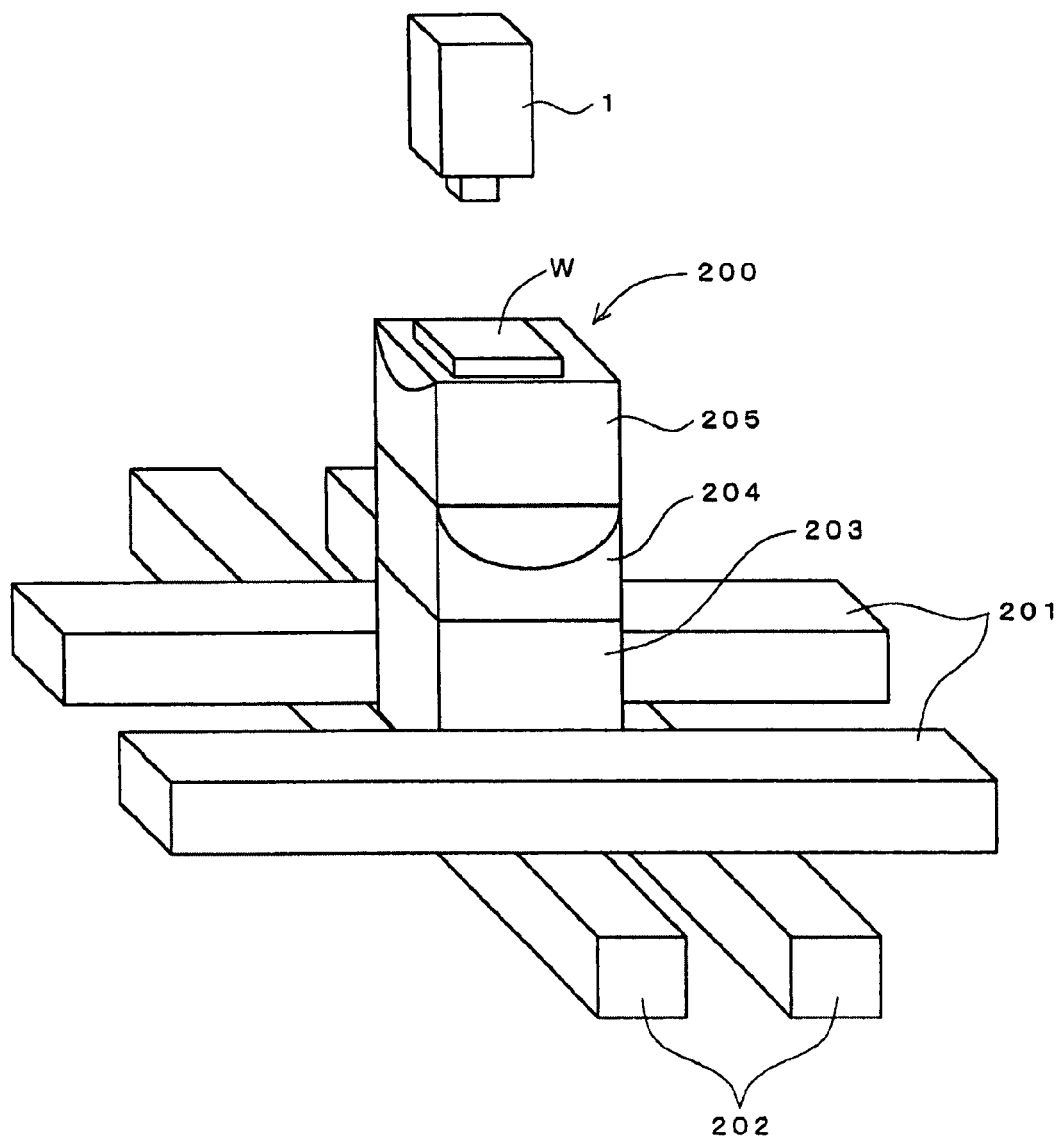
FIG. 21 is an external view of another inspection device according to a different embodiment.

FIG. 21 shows another inspection device according to a different embodiment of the invention, characterized as having, instead of the robot 3, an object supporting device 200 with a plurality of stages 201-205 on which a target object W is to be supported. The camera 1 is affixed above the top stage 205 such that its optical axis is in the vertical direction. In the above, numeral 201 indicates an X-stage, numeral 202 indicates a Y-stage and numeral 203 indicates a Z-stage to be used for adjusting the position of the target object W. Numerals 204 and 205 indicate a gonio stage to be used for adjusting the orientation of the target object W. If the camera 1 is provided with an auto-focusing function or a function of adjusting the focus based on an instruction from the PLC 5, the Z-stage may be dispensed with.

Components other than the camera 1 and the object supporting device 200 are omitted from FIG. 21 but it is to be understood that an illuminator 2 as explained above with reference to FIG. 4 is disposed between them. A stage control device (not shown) for controlling the motion of the object supporting device 200, as well as a PLC 5 and a process control device 6 as described above, is also provided.

The inspection device shown in FIG. 21 also serves to adjust the position and orientation of the target object by controlling the operations of the stages 201-205 of the object supporting device 200 and to obtain images. As shown in FIGS. 10 and 17, furthermore, data for setting the position and orientation of the target object and the target inspection areas are determined and registered in the process control device 6.

What is claimed is:

1. A method of inspecting condition of a target surface of a target object, said target surface including portions having different curvatures, said method comprising the steps of:
carrying out a preparation for sequentially inspecting a plurality of target objects having a same shape;
obtaining an image of said target surface by regularly reflected light for a plurality of times by using an illuminating device and a camera that are fixed and by supporting said target object such that the position and orientation of said target object are variable; and
processing the obtained images of said target surface;
wherein said preparation comprises the steps of determining the position and orientation that are to be taken by each of said target objects at each of said plurality times and determining target inspection areas on the obtained images to thereby generate set data that represent results of the steps of determining;
wherein said image of said target surface is obtained by supporting said target object in the position and orientation according to said set data;
wherein the position and orientation of the target objects and said target inspection areas are determined such that each of said target inspection areas is determined as the area where the corresponding image by regularly reflected light is obtained or a portion of said area and that the image of any point on said target surface will be included in at least one of said target inspection areas of any of the images obtained in said plurality of times;
wherein said preparation is carried out by using said camera to obtain a model image of a model object considered to have no defects, supported such that the position and orientation of said model object are variable, said preparation being carried out by displaying said model image on a monitor;
wherein said preparation comprises carrying out a first setting unit process on a plurality of specified places on a target inspection surface of said model object serving as target object, said first setting unit process comprising:
step A of determining the position and orientation of said target object such that an image including the image by regularly reflected light of a specified place on a target inspection surface of said target object will be displayed on said monitor;
step B of determining the area on the image of said target area on which the image by regularly reflected light is obtained or a portion of the area as said target inspection area; and
step C of generating set data representing the position and orientation determined in the step A and the target inspection area determined in the step B; and
wherein said plurality of specified places are specified such that the image of said any point on said target surface is included in at least one of the plurality of target inspection areas determined by carrying out said first setting unit process.

2. A method of inspecting condition of a target surface of a target object, said target surface including portions having different curvatures, said method comprising the steps of:
carrying out a preparation for sequentially inspecting a plurality of target objects having a same shape;
obtaining an image of said target surface by regularly reflected light for a plurality of times by using an illuminating device and a camera that are fixed and by supporting said target object such that the position and orientation of said target object are variable; and
processing the obtained images of said target surface;
wherein said preparation comprises the steps of determining the position and orientation that are to be taken by each of said target objects at each of said plurality times and determining target inspection areas on the obtained images to thereby generate set data that represent results of the steps of determining;
wherein said image of said target surface is obtained by supporting said target object in the position and orientation according to said set data;
wherein the position and orientation of the target objects and said target inspection areas are determined such that each of said target inspection areas is determined as the area where the corresponding image by regularly reflected light is obtained or a portion of said area and that the image of any point on said target surface will be included in at least one of said target inspection areas of any of the images obtained in said plurality of times;
wherein said preparation is carried out by using design data representing three-dimensional shape of said target object;
wherein said preparation comprises carrying out a second setting unit process on a plurality of specified places on a target inspection surface of said target object, said second setting unit process comprises:
step a of using said design data and thereby obtaining the direction of the normal line to said target surface at a specified position;
step b of using said design data and thereby identifying an area on said target object where regularly reflected light can be made incident to said camera if said camera takes an image of said specified position on said target surface along said normal line;
step c of obtaining a regular reflection image area on said image taken in said step b, said regular reflection image area being the area on which the area on said target object identified in said step b appears;
step d of determining said regular reflection image area or a portion of said regular reflection image area as said target inspection area; and
step e of generating set data that represent the position and orientation of said target object identified by the position of said specified position and the direction of said normal line obtained in said step a and said target inspection area; and
wherein said plurality of specified places are specified such that the image of said any point on said target surface is included in at least one of the plurality of target inspection areas determined by carrying out said second setting unit process.

3. A device for inspecting condition of a target surface of a target object, said target surface including portions having different curvatures, said device comprising:
an illuminating device and a camera with fixed optical axes and focal distances;
a supporting device for supporting said target object such that the position and orientation of said target object are variable;
a monitor for displaying thereon a model image of a model object considered to have no defects; and
a control device for controlling the position and orientation of said target object as an image of said target object is obtained for a plurality of times by said camera and by illuminating with said illuminating device;
wherein the position and orientation of said target object are controlled such that the image of any point on said target surface will be included in at least one of the images obtained by said camera;

wherein said model image is obtained during a preparation which is carried out by using said camera and said model object is supported such that the position and orientation of said model object are variable, said preparation being carried out by displaying said model image on said monitor;

wherein said preparation comprises carrying out with the control device a first setting unit process on a plurality of specified places on a target inspection surface of said model object serving as target object, said first setting unit process comprising:

step A of determining the position and orientation of said target object such that an image including the image by regularly reflected light of a specified place on a target inspection surface of said target object will be displayed on said monitor;

step B of determining the area on the image of said target area on which the image by regularly reflected light is obtained or a portion of the area as said target inspection area; and step C of generating set data representing the position and orientation determined in the step A and the target inspection area determined in the step B; and wherein said plurality of specified places are specified such that the image of said any point on said target surface is included in at least one of the plurality of target inspection areas determined by carrying out said first setting unit process.

4. The device of claim 3 wherein said supporting device comprises an articulated robot arm having a plurality of shafts;

wherein said camera is fixed so as to be able of take images of said target object supported by said robot arm obliquely from above; and wherein said control device serves to attach said target object to an end position of said robot arm as said target object is supplied to a position below said camera and to move said attached target object to another position where said camera can take an image of said target object.

5. A device for inspecting condition of a target surface of a target object, said target surface including portions having different curvatures, said device comprising:

an illuminating device and a camera with fixed optical axes and focal distances;

a supporting device for supporting said target object such that the position and orientation of said target object are variable;

a monitor for displaying thereon a model image of a model object considered to have no defects; and a control device for controlling the position and orientation of said target object as an image of said target object is obtained for a plurality of times by said camera and by illuminating with said illuminating device;

wherein the position and orientation of said target object are controlled such that the image of any point on said target surface will be included in at least one of the images obtained by said camera;

wherein said model image is obtained during a preparation which is carried out by using said camera and said model object is supported such that the position and orientation of said model object are variable, said preparation being carried out by displaying said model image on said monitor;

wherein said model image is obtained during a preparation which is carried out by using design data representing three-dimensional shape of said target object;

wherein said preparation comprises carrying out with the control device a second setting unit process on a plurality of specified places on a target inspection surface of said target object, said second setting unit process comprises:

step a of using said design data and thereby obtaining the direction of the normal line to said target surface at a specified position;

step b of using said design data and thereby identifying an area on said target object where regularly reflected light can be made incident to said camera if said camera takes an image of said specified position on said target surface along said normal line;

step c of obtaining a regular reflection image area on said image taken in said step b, said regular reflection image area being the area on which the area on said target object identified in said step b appears;

step d of determining said regular reflection image area or a portion of said regular reflection image area as said target inspection area; and step e of generating set data that represent the position and orientation of said target object identified by the position of said specified position and the direction of said normal line obtained in said step a and said target inspection area; and wherein said plurality of specified places are specified such that the image of said any point on said target surface is included in at least one of the plurality of target inspection areas determined by carrying out said second setting unit process.

6. The device of claim 5 wherein said supporting device comprises an articulated robot arm having a plurality of shafts;

wherein said camera is fixed so as to be able of take images of said target object supported by said robot arm obliquely from above; and wherein said control device serves to attach said target object to an end position of said robot arm as said target object is supplied to a position below said camera and to move said attached target object to another position where said camera can take an image of said target object.

* * * * *

UNITED STATES PATENT AND TRADEMARK OFFICE
CERTIFICATE OF CORRECTION

| | | |
|---|---|---|
| PATENT NO. | : 7,782,451 B2 | Page 1 of 1 |
| APPLICATION NO. | : 11/707293 | |
| DATED | : August 24, 2010 | |
| INVENTOR(S) | : Toshihiko Matsumoto et al. | |

It is certified that error appears in the above-identified patent and that said Letters Patent is hereby corrected as shown below:

On the Title Page:

Under Prior Publication Data, add the following section:

(30)        Foreign Application Priority Data
   March 10, 2006   (JP)............2006-066081

Signed and Sealed this
First Day of March, 2011

David J. Kappos
*Director of the United States Patent and Trademark Office*